(12) United States Patent
Diallo

(10) Patent No.: US 10,383,485 B2
(45) Date of Patent: Aug. 20, 2019

(54) SYSTEMS FOR MIMICKING ARM AND HAND MOVEMENT

(71) Applicant: Attaoulaye Diallo, Conakry (GN)

(72) Inventor: Attaoulaye Diallo, Conakry (GN)

( * ) Notice: Subject to any disclaimer, the term of this patent is extended or adjusted under 35 U.S.C. 154(b) by 4 days.

(21) Appl. No.: 15/270,481

(22) Filed: Sep. 20, 2016

(65) Prior Publication Data

US 2018/0078098 A1    Mar. 22, 2018

(51) Int. Cl.
| | |
|---|---|
| *A47K 3/28* | (2006.01) |
| *A47K 5/12* | (2006.01) |
| *A47K 7/00* | (2006.01) |
| *A47K 7/04* | (2006.01) |
| *A47K 7/08* | (2006.01) |
| *A61F 4/00* | (2006.01) |
| *E03C 1/18* | (2006.01) |
| *E03D 9/00* | (2006.01) |
| *A47K 10/00* | (2006.01) |
| *A47K 11/10* | (2006.01) |
| *A47K 13/14* | (2006.01) |
| *A47K 13/30* | (2006.01) |
| *A47K 17/00* | (2006.01) |
| *E03D 11/13* | (2006.01) |
| *E03D 13/00* | (2006.01) |

(52) U.S. Cl.
CPC ............ *A47K 7/04* (2013.01); *A47K 3/281* (2013.01); *A47K 5/1217* (2013.01); *A47K 7/00* (2013.01); *A47K 7/08* (2013.01); *A47K 11/10* (2013.01); *A47K 13/14* (2013.01); *A47K 13/302* (2013.01); *A47K 17/003* (2013.01); *A61F 4/00* (2013.01); *E03C 1/18* (2013.01); *E03D 9/00* (2013.01); *E03D 9/002* (2013.01); *E03D 13/005* (2013.01); *A47K 10/00* (2013.01); *A47K 17/00* (2013.01); *E03D 11/13* (2013.01)

(58) Field of Classification Search
CPC .. A47K 7/00; A47K 7/04; A47K 17/00; A61F 4/00; E03D 9/00; E03D 9/02
USPC ........................................................... 4/661
See application file for complete search history.

(56) References Cited

U.S. PATENT DOCUMENTS

| | | | |
|---|---|---|---|
| 6,817,641 | B1 | 11/2004 | Singleton, Jr. |
| 7,296,835 | B2 | 11/2007 | Blackwell et al. |
| 8,401,700 | B2 | 3/2013 | Ihrke et al. |
| 2010/0292842 | A1 | 11/2010 | Takahashi |

(Continued)

OTHER PUBLICATIONS

Bebionic (http://bebionic.com/distributor/documents/bebionic3_Tech_Manual_web.pdf) retrieved Sep. 2016.

(Continued)

*Primary Examiner* — Tuan N Nguyen
(74) *Attorney, Agent, or Firm* — Christopher P. Maiorana, PC

(57) ABSTRACT

An example system includes a manipulation device configured to be mounted to a sanitation apparatus for storing or disposing human waste. The manipulation device includes a first arm mechanism, a second arm mechanism, a first articulating joint mechanically coupling the first arm mechanism to the second arm mechanism, a grasping mechanism, and a second articulating joint mechanically coupling the second arm mechanism to the grasping mechanism. The system also includes a control module communicatively coupled to the manipulation device and configured to control the manipulation device.

15 Claims, 27 Drawing Sheets

(56) References Cited

U.S. PATENT DOCUMENTS

2014/0217762 A1    8/2014  Ihrke et al.

OTHER PUBLICATIONS

Engadget—KAR (http://www.engadeget.com/2008/12/18/kar-robot-arm-does-the-dishes-sort-of) retrieved Sep. 2016.
Engadget—Assistant Robot (https://www.engadget.com/2008/10/29/the-assistant-robot-cleans-almost-all-that-you-soil) retrieved Sep. 2016.
3D Madonnari (http://www.3d-madonnari.com/robot-chef-moley-replace-hostess-in-the-kitchen/) retrieved Sep. 2016.
Open Ideo (https://challenges.openideo.com/challenge/fighting-ebola/ideas/robot-arm-cleaning-infected-toilets-24-hours-a-day) retrieved Sep. 2016.
Advanced Arm Dynamics—New Technology (http://armdynamics.com/pages/new-technology) retrieved Sep. 2016.
Advanced Arm Dynamics—Bebionic (http://armdynamics.com/pages/bebionic) retrieved Sep. 2016.
Advanced Arm Dynamics—Finger and Partial Hand (http://armdynamics.com/pages/electric-partial-hand) retrieved Sep. 2016.
Advanced Arm Dynamics—i-Limb (http://armdynamics.com/pages/i-limb-quantum) retrieved Sep. 2016.
Advanced Arm Dynamics—Michelangelo (http://armdynamics.com/pages/michelangelo) retrieved Sep. 2016.
Advanced Arm Dynamics—TMR (http://armdynamics.com/pages/tmr) retrieved Sep. 2016.

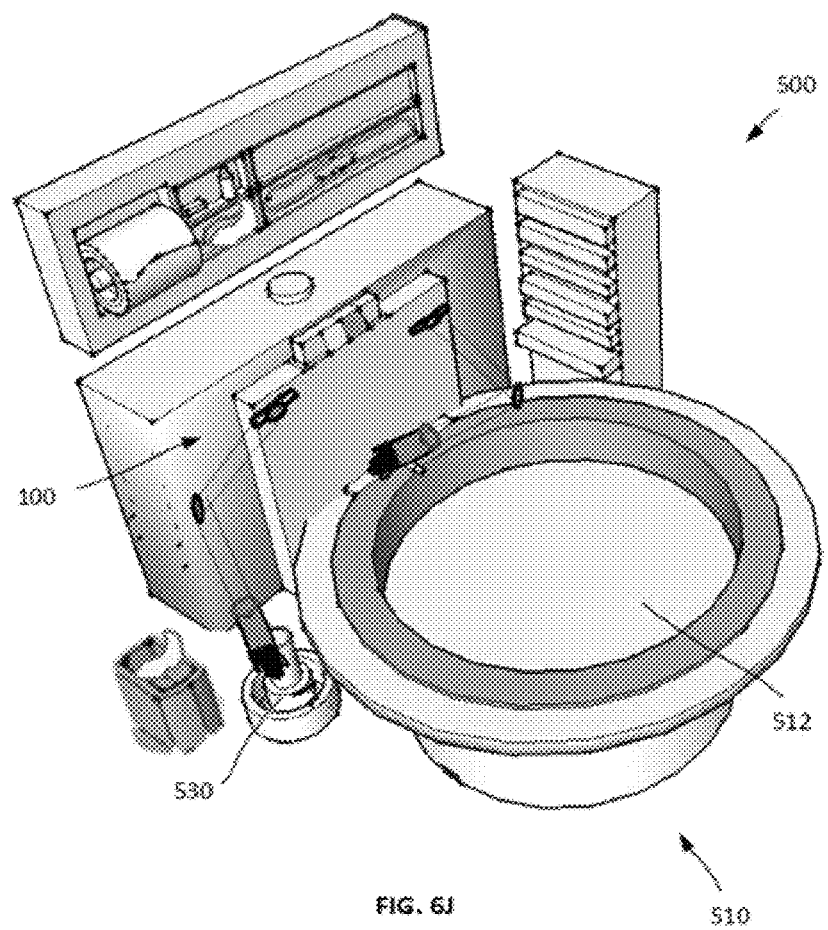

SYSTEMS FOR MIMICKING ARM AND HAND MOVEMENT

TECHNICAL FIELD

This disclosure relates to systems for mimicking the movement of a human arm and/or hand.

BACKGROUND

People use their arms and hands to touch, grasp, and manipulate objects and things. In many cases, this enables people to perform a variety of tasks. For example, people often use their arms and hands to pick up and carry physical items, reposition and reorient physical items, utilize tools, and support themselves, among other physical activities.

In some cases, people may partially or fully lose the use of one or more of their arms and/or hands. For example, a person may suffer from an injury that impairs the use of one or both of their hands and/or arms. As another example, a person may be born with an impairment to one or both of his hands and/or arms. In these situations, a person may find it more difficult to perform certain physical activities.

Due to physical limitations, people also may find it difficult to perform certain tasks with their own arms and hands. For example, as arms and hands have a limited span and range of motion, people may find it difficult to reach certain areas of their body (e.g., their backs). As another example, people may find it difficult to reach areas that are distant from their body (e.g., locations that are higher or lower than their current location, and out of the reach of their arms and hands). As another example, as people typically have two arms and two hands, a person may find it difficult to perform many tasks at once (e.g., touching, grasping, and/or manipulating several objects simultaneously). As another example, certain objects may be too heavy, large, and/or burdensome for a person to manipulate with their own arms and hands.

In some cases, human may also find it inconvenient or unsanitary to perform certain tasks with their own arms and hands. For example, certain tasks can soil arms and hands (e.g., activities involving touching dirty objects), which may be uncomfortable or unsafe. As another example, certain tasks may be uninteresting or mundane to perform manually.

SUMMARY

In general, in an aspect, a system includes a manipulation device configured to be mounted to a sanitation apparatus for storing or disposing human waste. The manipulation device includes a first arm mechanism, a second arm mechanism, a first articulating joint mechanically coupling the first arm mechanism to the second arm mechanism, a grasping mechanism, and a second articulating joint mechanically coupling the second arm mechanism to the grasping mechanism. The system also includes a control module communicatively coupled to the manipulation device and configured to control the manipulation device.

Implementations of this aspect can include one or more of the following features.

In some implementations, the control module can be configured to operate the manipulation device according to a first cleaning phase. During the first cleaning phase the manipulation device can be configured to grasp a first wiping sheet with the grasping mechanism, position the first wiping sheet against a part of a user's body, drag the first wiping sheet one or more times against the part of the user's body, and release the first wiping sheet into a basin of the sanitation apparatus.

In some implementations, the control module can be further configured to operate the manipulation device according to a second cleaning phase. During the second cleaning phase the manipulation device can be configured to grasp a second wiping sheet with the grasping mechanism, the second wiping sheet being moistened with a first cleaning agent, position the second wiping sheet against the part of the user's body, drag the second wiping sheet one or more times against the part of the user's body, and release the second wiping sheet into the basin of the sanitation apparatus.

In some implementations, the control module can be further configured to operate the manipulation device according to a third cleaning phase. During the third cleaning phase the manipulation device can be configured to grasp a third wiping sheet with the grasping mechanism, the third wiping sheet being substantially dry, position the third wiping sheet against the part of the user's body, drag the third wiping sheet one or more times against the part of the user's body, release the third wiping sheet into the basin of the sanitation apparatus, and operate a flushing mechanism of the sanitation apparatus.

In some implementations, the control module can be further configured to operate the manipulation device according to a fourth cleaning phase. During the fourth cleaning phase the manipulation device can be configured to grasp a cleaning tool with the grasping mechanism, apply a second cleaning agent to the cleaning tool, and drag the cleaning tool one or more times across one or more surfaces of the sanitation apparatus.

In some implementations, the control module can be further configured to repeat at least one of the first cleaning phase, the second cleaning phase, the third cleaning phase, and/or the fourth cleaning phase one or more times.

In some implementations, the grasping mechanism can include one or more articulating fingers.

In some implementations, the first arm mechanism can be configured to be mounted to the sanitation apparatus through a third articulating joint.

In some implementations, the manipulation device can further include a third arm mechanism, a fourth arm mechanism, a fourth articulating joint mechanically coupling the third arm mechanism to the fourth arm mechanism, a second grasping mechanism, and a fifth articulating joint mechanically coupling the fourth arm mechanism to the second grasping mechanism.

In some implementations, the manipulation device can further include a sixth articulating joint. The third arm mechanism can be configured to be mounted to the sanitation apparatus through the sixth articulating joint.

In some implementations, the manipulation device can be mounted above a basin of the sanitation apparatus.

In some implementations, the control device can include an electronic control module configured to transmit electronic control signals to the manipulation device. The manipulation device can be configured to automatically operate in response to receiving the electronic control signals.

In some implementations, the control device can include a mechanical mechanism. The manipulation device can be configured to operate in response to a user manipulating the mechanical mechanism.

In some implementations, the sanitation apparatus can be a toilet.

In some implementations, the sanitation apparatus can be a urinal.

In general, in another aspect, a system includes a manipulation device configured to be mounted to a body cleaning apparatus. The manipulation device includes a first arm mechanism, a second arm mechanism, a first articulating joint mechanically coupling the first arm mechanism to the second arm mechanism, a grasping mechanism, and a second articulating joint mechanically coupling the second arm mechanism to the grasping mechanism. The system also includes a control module communicatively coupled to the manipulation device and configured to control the manipulation device.

Implementations of this aspect can include one or more of the following features.

In some implementations, the body cleaning apparatus can include a sink or a shower.

In some implementations, the control module can be configured to operate the manipulation device according to a first cleaning phase. During the first cleaning phase, the manipulation device can be configured to apply a portion of soap onto a user's body using the grasping mechanism, and rub the user's body with the grasping mechanism.

In some implementations, the control module can be configured to operate the manipulation device according to a second cleaning phase. During the second cleaning phase, the manipulation device can be configured to grasp a towel using the grasping mechanism, position the towel against the user's body using the grasping mechanism, and rub the towel against the user's body one or more times using the grasping mechanism.

In some implementations, the control module can be configured to operate the manipulation device according to a third cleaning phase. During the third cleaning phase, the manipulation device can be configured to grasp a cleaning tool with the grasping mechanism, apply a cleaning agent to the cleaning tool, and drag the cleaning tool one or more times across one or more surfaces of the body cleaning apparatus.

The details of one or more implementations are set forth in the accompanying drawings and the description below. Other features, objects, and advantages will be apparent from the description and drawings, and from the claims.

DETAILED DESCRIPTION

Figure 1:
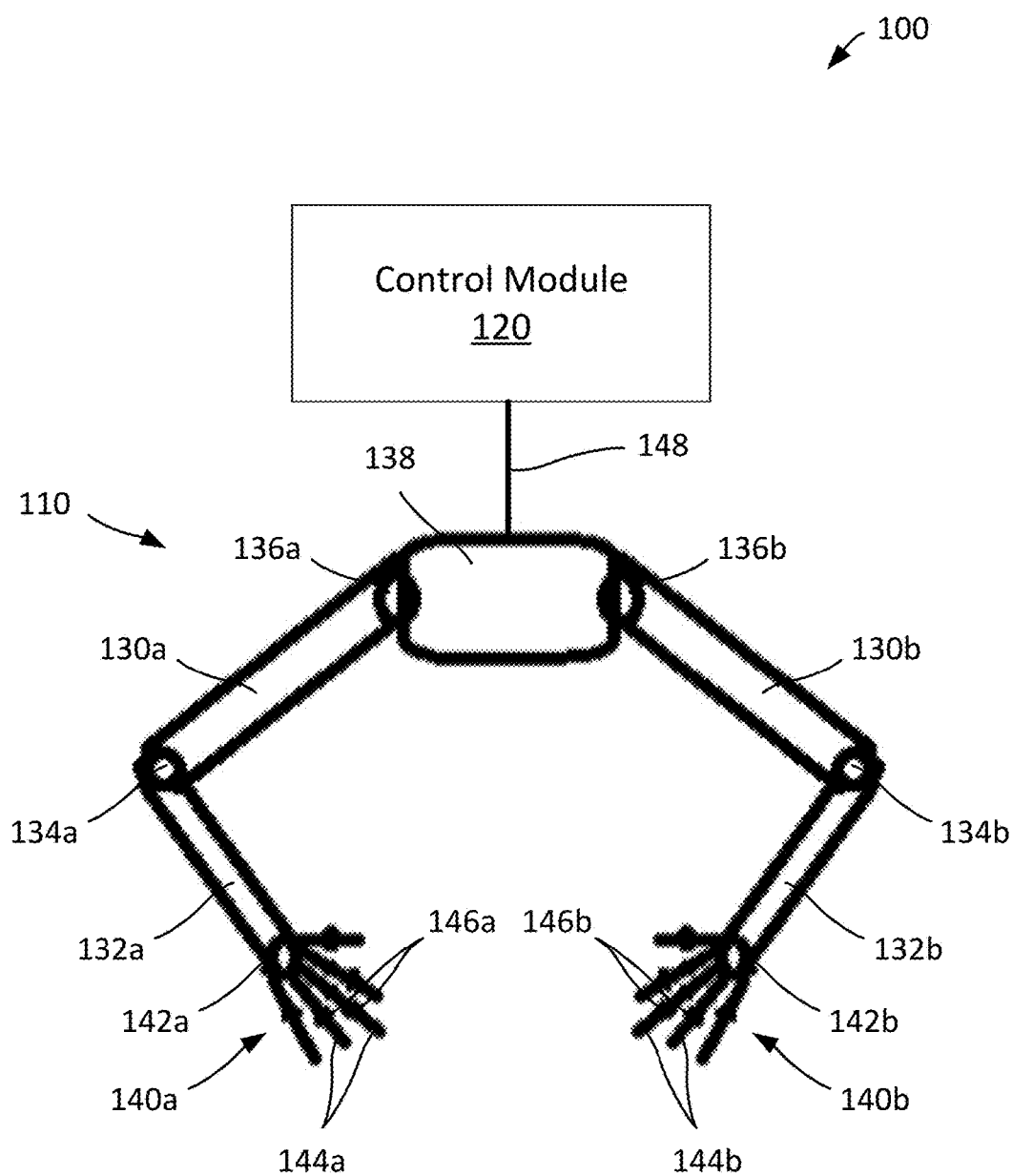
FIG. 1 is a diagram of an example system for mimicking arm and hand movement.

An example system 100 for mimicking arm and hand movement is shown in FIG. 1. Implementations of the system 100 can be used to perform a variety of physical tasks. As an example, implementations of the system 100 can assist a user in utilizing and/or maintaining a sanitation apparatus for storing or disposing human waste (e.g., a toilet or a urinal). As another example, implementations of the system 100 can assist a user in utilizing and/or maintaining an apparatus used for washing or bathing (e.g., a sink or a shower).

In some cases, implementations of the system 100 enable a user to perform physical activities (e.g., urinating, defecating, washing, bathing, and housekeeping) in a manner that reduces the use of his own arms and hands. As an example, implementations of the system 100 automatically can cleanse parts of the user's body, such that the user need not manually cleanse those parts of his body with his own arms and hands. As another example, implementations of the system 100 can automatically cleanse the surrounding environment (e.g., a toilet, a urinal, a sink, or a shower), such that the user need not manually cleanse the surrounding environment with his own arms and hands. This can be beneficial, for example, as it enables physically disabled users (e.g., users who have partially or fully lost the use of one or more of their arms and/or hands) to perform various physical tasks more easily. This can also be beneficial, for example, as it enables users to conduct various physical tasks more conveniently (e.g., by reducing the user's manual involvement in those tasks) and/or in a more sanitary manner (e.g., by reducing the user's physical contact with unsanitary materials, such as dirt, human waste, or other filth). This can also be beneficial, for example, as it enables the user to clean and maintain facilities such as toilets, urinals, sinks, and showers more easily and efficiently. This can also be beneficial, for example, as it enables the user to reduce or prevent the spread of contagious diseases (e.g., diseases that can be spread by contact with human waste).

As shown in FIG. 1, the system 100 includes a manipulation device 110 and a control module 120. A portion of the manipulation device 110 is shown in greater detail in FIG. 2.

The manipulation device 110 articulates to touch, grasp, and/or manipulate objects and things. As described herein, the manipulation device 110 can mimic the physical movements of human arms and hands. For example, in some cases, the manipulation device 110 can be configured to reach towards to one or more objects, grasp those objects, reposition those objects to one or more new locations, and release those object at the new locations.

Figure 2:
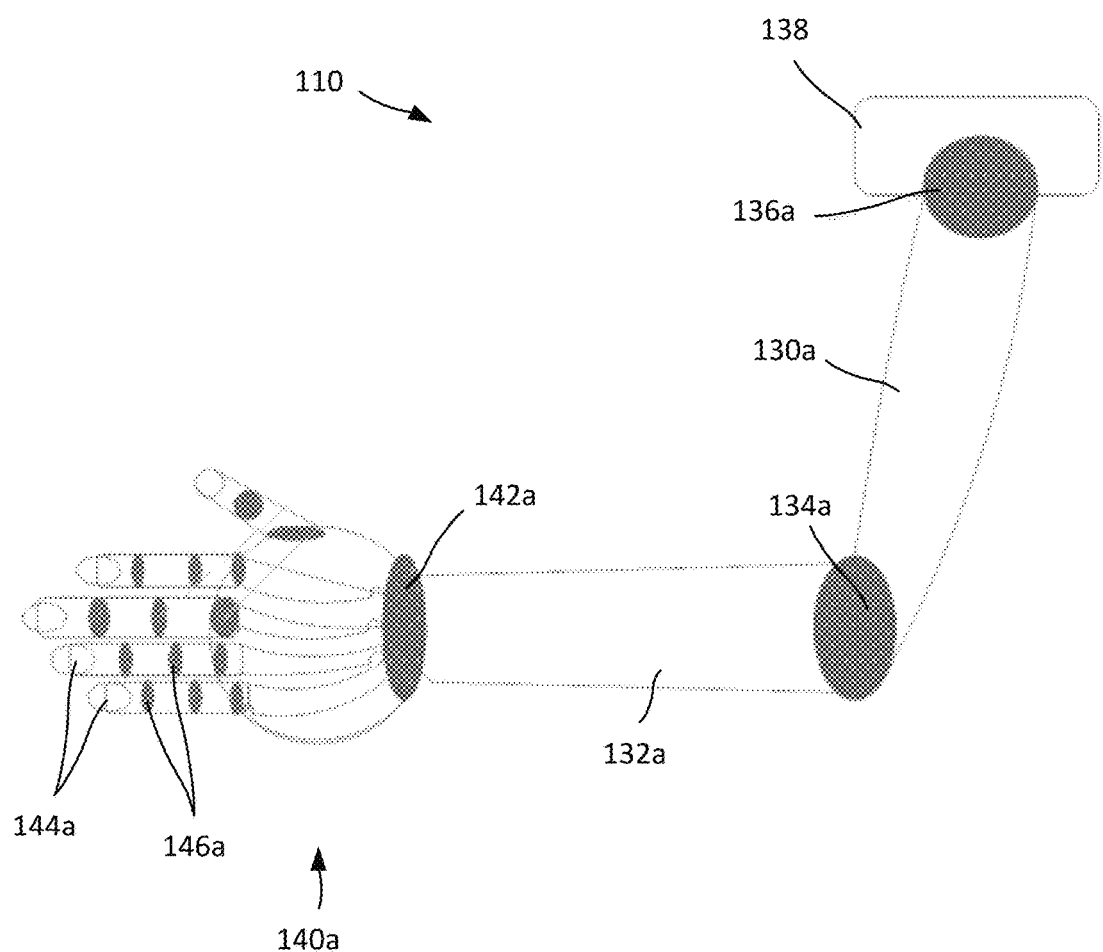
FIG. 2 is a diagram of a portion of an example manipulation device.

The manipulation device 110 shown in FIGS. 1 and 2 includes an arm mechanism 130*a* and an arm mechanism 132*a*. An articulating joint 134*a* mechanically couples the arm mechanisms 130*a* and 132*a*, and an articulating joint 136*a* mechanically couples the arm mechanism 130*a* to a base 138.

As shown in FIGS. 1 and 2, each of the arm mechanisms 130*a* and 132*a* can extend substantially along a respective direction (e.g., a respective axis of extension). In some cases, the arm mechanisms 130*a* and 132*b* can include one or more axially extending components, such as bars, beams, shafts, or rods. The length of each of the arm mechanisms 130*a* and 132*b* can vary. In some cases, the length of the arm mechanism 130*a* can be between approximately 5 cm to 49 cm, and the length of the arm mechanism 132a can be between approximately 5 cm to 49 cm.

The articulating joint 134a enables the arm mechanisms 130a and 132a to reposition and/or reorient themselves with respect to one another. For example, in some cases, the articulating joint 134a can include one or more ball and socket joints, hinge joints, condyloid joints, pivot joints, gliding joints, saddle joints, or other types of joints that enable the arm mechanisms 130a and 132a to move and/or reorient with respect to one another in one or more degrees of freedom.

In a similar manner, the articulating joint 136a enables the arm mechanism 130a to reposition and/or reorient itself with respect to the base 138. For example, in some cases, the articulating joint 136a can include one or more ball and socket joints, hinge joints, condyloid joints, pivot joints, gliding joints, saddle joints, or other types of joints that enable the arm mechanism 130a to move and/or reorient with respect to the base 138 in one or more degrees of freedom.

Movement of the arm mechanisms 130a and 132a can be provided, for example, by one or more motors and/or actuators mechanically coupled to the arm mechanisms 130a and 132a. For example, one or more motors and/or actuators can be mechanically coupled to the arm mechanisms 130a and/or 132a, such that one arm mechanism 130a or 132a can be repositioned and/or reoriented relative to the other arm mechanism 130a or 132a and/or the base 138.

The manipulation device 110 also includes a grasping mechanism 140a and an articulating joint 142a mechanically coupling the grasping mechanism 140a to the arm mechanism 132a.

The grasping mechanism 140a is configured to physically grip objects. As shown in FIGS. 1 and 2, the grasping mechanism 140a includes several finger mechanisms 144a, each of which are configured to curl and uncurl through articulating joints 146a. This range of motion can be used, for example, to clench an object (e.g., by curling the finger mechanisms 144a around the object), release an object (e.g., by uncurling the finger mechanisms 144a away from the object), pinch an object (e.g., by curling the finger mechanisms 144a such that they contact opposing sides of the object), and so forth. In some case, this range of motion also enables the grasping mechanism 140a to take on certain physical forms, such as a relatively flat form (e.g., by extending each of the finger mechanisms 144a along a substantially common plane), a relatively rounded form (e.g., by curling each of the finger mechanisms 144a into one another), and so forth. The length of each of the finger mechanisms 144a can vary. In some cases, the length of each of the finger mechanisms 144a can be between approximately 2 cm and 5 cm. Although five finger mechanisms 144a are shown in FIG. 1, this is merely an illustrative example. In practice, there may be any number of finger mechanisms 144a (e.g., one, two, three, four, or more), depending on the implementation.

In some cases, the grasping mechanisms 140a can include one or more axially extending components, such as bars, beams, shafts, or rods. For example, each finger mechanisms 144a can be implemented using one or more bars, beams, shafts, or rods, and the finger mechanisms 144a can be physically coupled together to form a portion of or the entirety of the grasping mechanism 140a. In some cases, each articulating joint 146a can include one or more ball and socket joints, hinge joints, condyloid joints, pivot joints, gliding joints, saddle joints, or other types of joints that enable the components of the grasping mechanism 140a to move and/or reorient with respect to one another in one or more degrees of freedom.

The articulating joint 142a enables the arm mechanism 132a and the grasping mechanism 140a to reposition and/or reorient themselves with respect to one another. For example, in some cases, the articulating joint 142a can include one or more ball and socket joints, hinge joints, condyloid joints, pivot joints, gliding joints, saddle joints, or other types of joints that enable the arm mechanism 132a and the grasping mechanism 140a to move and/or reorient with respect to one another in one or more degrees of freedom.

Movement of the grasping mechanism 140a can be provided, for example, by one or more motors and/or actuators mechanically coupled to the grasping mechanism 140a. For example, one or more motors and/or actuators can be mechanically coupled to the one or more of the finger mechanisms 144a, such that finger mechanisms 144a perform a curling or uncurling motion. As another example, one or more motors and/or actuators can be mechanically coupled to the grasping mechanism 140a, such that grasping mechanism 140a can be repositioned and/or reoriented relative to the arm mechanism 132a.

The movement of the arm mechanisms 130a and 132a and the grasping mechanism 140a are controlled by the control module 120. For instance, the control module 120 can include one or more electronic control modules that transmit electronic control signals to regulate the movement of one or more motors and/or actuators of the system 100. As an example, the control module 120 can selectively transmit electronic control signals instructing particular motors and/or actuators to turn on or off, generate a particular type of movement, generate a particular magnitude of movement, operate at a particular speed, and so forth. This enables the control module 120 to precisely control the position and/or orientation of each component of the system 100.

In some cases, the control module 120 can assign each articulating joint 134a, 136a, 142a, and/or 146a a respective unique identifier (e.g., a logical control address). This unique identifier enables the control module 120 to transmit electronic control signals invoking movements with respect to specific articulating joints in a selective manner. As an example, the motors and/or actuators that are configured to change the relative position and/or orientation of the arm mechanism 130a and 132b about the articulating joint 134a can be assigned a first unique identifier, and the control module 120 can transmit electronic control signals containing the first unique identifier to articulate the manipulation device 110 about the articulating joint 134a. Further, the motors and/or actuators that are configured to change the relative position and/or orientation of the arm mechanism 130a and base 138 about the articulating joint 136a can be assigned a second unique identifier, and the control module 120 can transmit electronic control signals containing the second unique identifier to articulate the manipulation device 110 about the articulating joint 136a. In this manner, the control module 120 can selectively control the position and/or orientation of each component of the system 100 with respect to specific articulating joints.

In some cases, some or all of the motors and/or actuators can be communicatively coupled to the control module 120 via a common communications bus 148. Each of the motors and/or actuators can monitor the electronic control signals transmitted across the communications bus 148, identify electronic control signals that pertain to it (e.g., electronic control signals having a particular unique identifier), and selectively operate in response to those identified electronic control signals.

In some cases, some or all of the motors and/or actuators can each be communicatively coupled to the control module 120 via a respective individual communications bus 148 (e.g., a dedicated wire or communications channel). Each of the motors and/or actuators can monitor its corresponding communications bus 148, and operate in response to any electronic control signals received from that communications bus 148.

In some cases, one or more of the components of the system 100 can have a default position and/or orientation, such that in the absence of specific instructions from the control module 120, those components each return to their default position and/or orientation. In some cases, each components default position and/or orientation can be referred to as its "resting" position.

In some cases, the control module 120 can operate in accordance to commands issued by a user. For example, the control module 120 can include one or more physical mechanisms (e.g., buttons, switches, levers, touch-sensitive input devices, etc.), motion-activated mechanisms (e.g., motion sensors, infrared sensors, light sensors, etc.), and/or audio-activated mechanism (e.g., microphones that enable the control module 120 to detect and interpret spoken commands from the user).

In some cases, the control module 120 can be positioned, either partially or fully, within the base 138. In some cases, the control module 120 can be positioned exterior to the base 138 (e.g., in a separate enclosure).

As shown in FIGS. 1 and 2, the arm mechanism 130a and 132a and the grasping mechanism 140a are successively coupled to one another, such that the grasping mechanism 140a can be positioned in a variety of locations and/or orientations. This enables the grasping mechanism 140a to touch, grasp, and manipulate objects and things that are within a particular distance from the base 138. In some cases, this action mimics the functionality of a human arm and hand.

In some cases, one or more of the articulating joints 134a, 136a, 142a, and/or 146a can selectively locked and unlocked, such that the relative position between some or all of the components of the system 100 can be selectively set or fixed for a period of time. This can be useful, for example, as it enables the system 100 to maintain a substantially stable and static relative position and/or orientation between the two or more of its components (e.g., when performing a physical task that does not require movement between the two components during a particular period of time).

In some cases, one or more of the articulating joints 134a, 136a, 142a, and/or 146a can include an internal control system that regulates the operation of the articulating joint. In some case, the internal control system can store information such as the current position of the articulating joint (e.g., the relative of the two or more components interconnected at the articulating joint), and the default or resting position of the articulating joint. Further, the internal control system can compare the current position of the articulating joint to a pre-defined limit (e.g., a threshold bending or rotation angle), and prevent the articulating joint from moving beyond the pre-defined limit. This can be useful, for example, in preventing the articulating joint from extending between its safe range of motion and reducing the likelihood of mechanical failure.

In some cases, the system 100 can include one or more touch-sensitive or contact-sensitive sensors that detect when one or more of the components come into contact with an object or the physical environment. The location of each sensor can vary, depending to the implementation. Information from these sensors can be transmitted to the control module 120, such that the movement of the manipulation device 110 can be more accurately controlled with respect to the object or the physical environment. For example, in some cases, one or more sensors can be placed various surfaces of the manipulation device 110 (e.g., on one or more of the finger mechanisms 144a), such that they can detect when the manipulation device 110 comes into contact with an object or the physical environment. Information from these sensors can be transmitted to the control module 120, such that the control module 120 can more accurately control the manipulation device 110 (e.g., by directing the manipulation device 110 towards a detected object to interact with it, by directing the manipulation device 110 away from the detected object to avoid it, and so forth). In some cases, a sensor can include a push-button mechanism to detect touch or contact with an object or the physical environment. For example, when the sensor comes into physical contact with an object or the physical environment, the push-button mechanism can be physically actuated by the contact. In response, the sensor determines that the push-button mechanism has been actuated (e.g., depressed), and transmits sensor information to the control module 120 indicating that the sensor has detected an object or the physical environment.

In some cases, the system 100 can include multiple sets of arm mechanisms and grasping mechanisms. This can be useful, for example, to mimic the functionality of multiple human arms and hands. For example, as shown in FIG. 1, the system 100 can include a second set of arm mechanisms 130b and 132b, grasping mechanism 140b having fingers mechanisms 144b, and articulating joints 134b, 136b, 142b and 146b. Each of these components can operate in a manner similar to the corresponding components of the first set, such that they mimic the functionality of a second human arm and hand. Although two sets of components are depicted in FIG. 1, this is merely an illustrative example. In practice, the system 100 can include any number of sets of components (e.g., one, two, three, four, or more) to mimic the functionality of any number of human arms and hands.

Figure 3A:
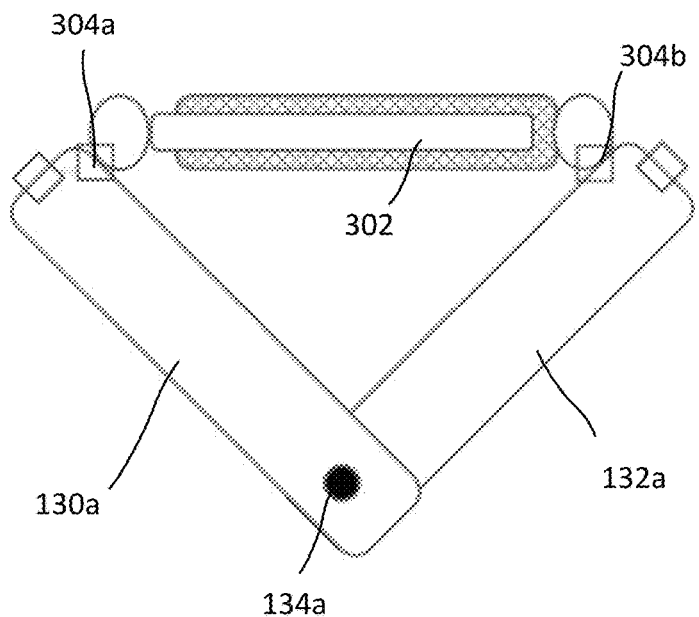
FIGS. 3A and 3B are diagrams showing the operation of an example articulating joint.

The articulating joints 134b, 136b, 142b and 146b can include one or more different types of joints. To illustrate, FIG. 3A shows an example articulating joint 134a that mechanically couples the arm mechanisms 130a and 132a (e.g., having a pin and socket arrangement). In this example, the articulating joint 134a is a hinge joint that enables the arm mechanisms 130a and 132a to move with respect to each another with a single degree of freedom (e.g., by swinging about the articulating joint 134a on a single plane).

As shown in FIG. 3A, the arm mechanisms 130a and 132a can be moved with respect to each another through an actuator 302 mechanically coupled to the arm mechanisms 130a and 132a at points 304a and 304b, respectively. For instance, as shown FIG. 3A when the actuator 302 is in a shorted state, the actuator 302 draws the point 304a of the arm mechanism 130 and the point 304b of the arm mechanism 132a towards each other. This results in a swinging movement of the arm mechanisms 130a and 132a about the articulating joint 134a (e.g., mimicking the flexing of an arm).

Figure 3B:
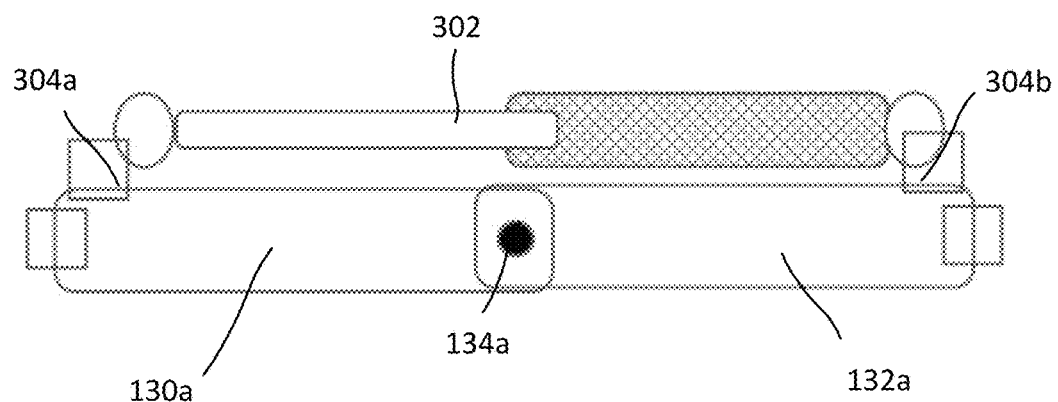

As shown FIG. 3B when the actuator 302 is in an elongated or lengthened state, the actuator 302 pushes the points 304a-b away from each other. This results in a swinging movement of the arm mechanisms 130a and 132a in an opposite direction about the articulating joint 134a (e.g., mimicking the extension of an arm). In some cases, the actuator 302 can be operated based on electronic control signals received from the control module 120.

Figure 4A:
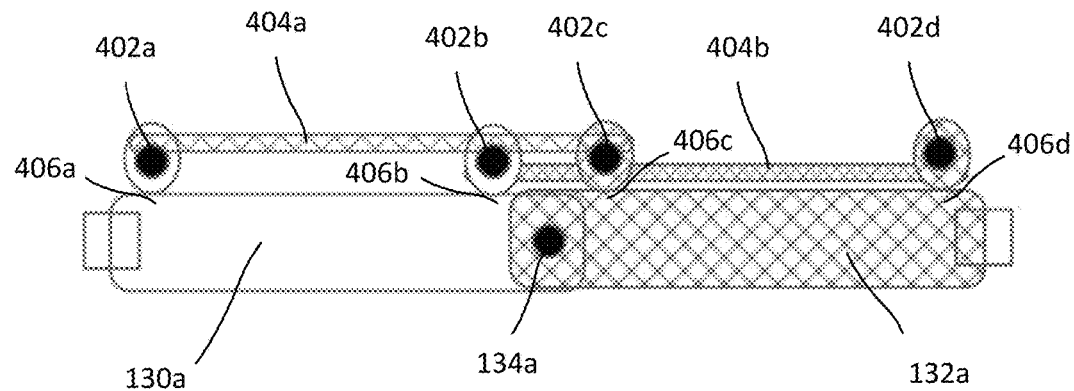
FIGS. 4A and 4B are diagrams showing the operation of another example articulating joint.

FIG. 4A shows another example articulating joint 134a that mechanically couples the arm mechanisms 130a and 132a. In this example, the articulating joint 134a is a hinge joint (e.g., having a pin and socket arrangement) that enables the arm mechanisms 130a and 132a to move with respect to each another with a single degree of freedom (e.g., by swinging about the articulating joint 134a on a single plane).

As shown in FIG. 4A, the arm mechanisms 130a and 132a can be moved with respect to each another through motors 402a-d and connective mechanisms 404a-b mechanically coupled to the arm mechanisms 130a and 132a. In this example, the motor 402a is mechanically coupled to the arm mechanism 130a at a point 406a, the motor 402b is mechanically coupled to the arm mechanism 130a at a point 406b, the motor 402c is mechanically coupled to the arm mechanism 132a at a point 406c, and the motor 402d is mechanically coupled to the arm mechanism 132a at a point 406d. The connective mechanism 404a is mechanically coupled to the motors 402a and 402c, and its effective length can be shorted or lengthen by operating the motors 402a and 402c (e.g., by spooling or winding the connective mechanism 404a about one or more rotational shafts of the motors 402a and 402c. Similarly, the connective mechanism 404b is mechanically coupled to the motors 402b and 402d, and its effective length can be shorted or lengthen by operating the motors 402b and 402d (e.g., by spooling or winding the connective mechanism 404b about one or more rotational shafts of the motors 402b and 402d.

As shown FIG. 4A when each of the connective mechanisms 404a-b is in a lengthened or relaxed state (e.g., when the connective mechanisms 404a-b are in a relatively unspooled or unwound state), the points 304a-b of the arm mechanisms 130a and 132a can be relatively distant from each other (e.g., mimicking the extension of an arm). In some cases, the articulating joint 134a can be biased towards this direction (e.g., through a spring or other biasing mechanism), such that absent external forces, it places the arm mechanisms 130a and 132a in this extended position.

Figure 4B:
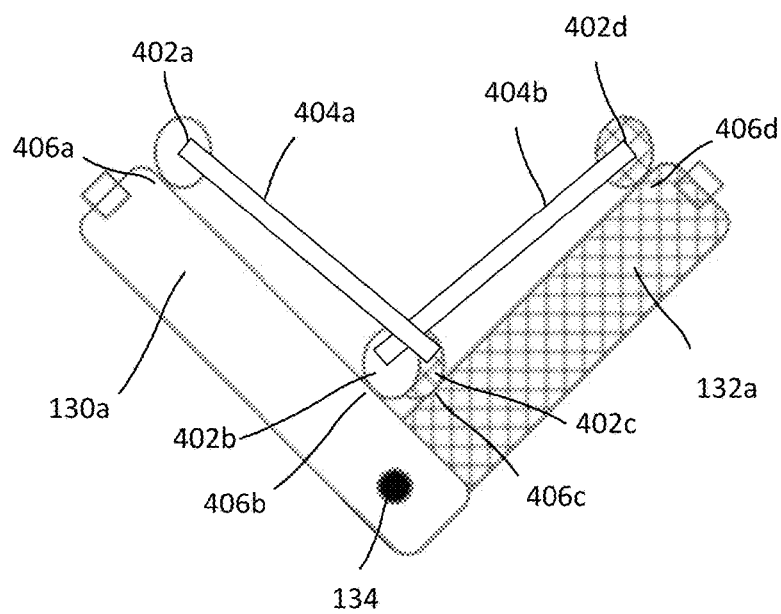

As described above, the motors 402a-d can be operated to shorten the effective length of the connective mechanisms 404a-b. For example, as shown in FIG. 4B, the motors 402a and 402c can be operated to shorten the effective length of the connective mechanism 404a (e.g., by spooling or winding the connective mechanism 404a about one or more shafts of the motors 402a and 402c). Further, the motors 402b and 402d can be operated to shorten the effective length of the connective mechanism 404b (e.g., by spooling or winding the connective mechanism 404b about one or more shafts of the motors 402b and 402d). As a result, point 406a of the arm mechanism 130a is drawn closer to point 406c of the arm mechanism 132b, and point 406b of the arm mechanism 130a is drawn closer to point 306d of the arm mechanism 132b. This results in a swinging movement of the arm mechanisms 130a and 132a about the articulating joint 134a (e.g., mimicking the flexing of an arm). In some cases, the motors 402a-d can be operated based on electronic control signals received from the control module 120.

Although examples of articulating joints are shown in FIGS. 3A, 3B, 4A, and 4B with respect to arm mechanisms 130a and 132a, similar articulating joints also can be used with respect to any of the other components of the manipulation device 110. Further, although example articulating joints are shown, in practice, other types of articulating joints also can be used, either instead of or in addition to those described.

As described herein, implementations of the system 100 can be used to perform a variety of physical tasks. For instance, implementations of the system 100 can assist a user in utilizing and/or maintaining a sanitation apparatus for storing or disposing human waste (e.g., a toilet or a urinal).

Figure 5:
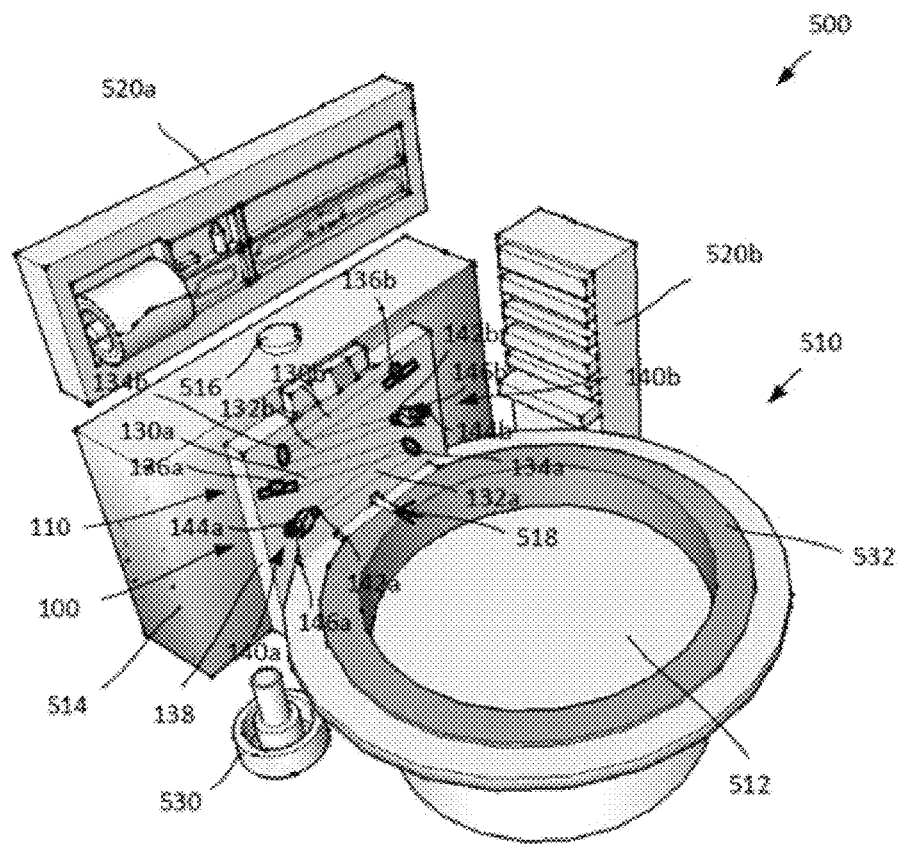
FIG. 5 is a diagram of an example sanitation system.

As an example, FIG. 5 shows a sanitation system 500 for storing or disposing of human waste. The system 500 includes a toilet 510, supply containers 520a-b, and a cleaning tool 530. The system 500 also includes a system 100 for mimicking arm and hand movement (e.g., as shown and described with respect to FIGS. 1 and 2).

The toilet 510 is a sanitation fixture used for the storing or disposal of human waste (e.g., urine and feces). The toilet 510 includes a basin 512 for collecting human waste, and a tank 514 for holding and dispensing water into the basin 512 (e.g., to aid in the collection and disposal of human waste in the basin 512).

The toilet 510 also includes a flushing mechanism 516 to control the operation of the toilet 510. When the flushing mechanism 516 is activated (e.g., by pressing a button or manipulating a lever), the contents of the basin 512 are cleared from the basin 512 (e.g., through a tube, pipe, or other conduit in fluid communication with a sewage or septic system), thereby disposing of any human waste collected by the basin 512. Further, clean water from the tank 514 is transferred to the basin 512 and the tank 514 is refilled with clean water (e.g., through a tube, pipe, or other conduit in fluid communication with a water source), such that the toilet 510 can be used again.

The toilet also includes a faucet 518 for dispensing water. The faucet 518 can be used, for example, to cleanse a user's body and/or cleanse the toilet 510 after use. In some cases, the faucet 518 can dispense water contained within the tank 514. In some cases, the faucet 518 can dispense water from a separate source (e.g., through a tube, pipe, or other conduit in fluid communication with a water source).

The supply containers 520a-b each contain objects or consumable items that facilitate use and/or maintenance of the system 500. For example, the supply containers 520a-b can contain toilet tissue, towels, cleaning agents (e.g., soap, disinfectants, bleach, cleaning solutions, cleaning powders, etc.), gloves, disposable covers or protectors, tarps, and so forth.

The cleaning tool 530 includes implements that facilitate maintenance of the system 500. For example, the cleaning tool 530 can include one or more toilet brushes, sponges, and scrubbing tools that can be used to cleanse the toilet 510.

The system 500 also includes a system 100 for mimicking arm and hand movement. As described above, the system 100 can be similar to that shown and described with respect to FIGS. 1 and 2. For example, as shown in FIG. 5, the system 100 can include a first set of arm mechanisms 130a and 132a, grasping mechanism 140a having fingers mechanisms 144a, and articulating joints 134a, 136a, 142a, and 146a (referencing FIG. 1). The system can also include a second set of arm mechanisms 130b and 132b, grasping mechanism 140b having fingers mechanisms 144b, and articulating joints 134b, 136b, 142b and 146b. In some cases, these two sets of components can mimic the functionality of two human arms and two human hands.

The system 100 can be mounted to the toilet 510, such that the system 100 can access one or more of the components of the system 500. For example, as shown in FIG. 5, the system 100 can be mounted such that its base 138 is secured to the tank 514 above the basin 512.

Although an example position for the system 100 is shown, this is merely an illustrative example. In practice, the system 100 can be secured and/or positioned at different locations, depending on the implementation. For example, in some cases, some or all of the system 100 can be positioned within the basin 512.

Further, although FIG. 5 shows an example in which the manipulation device 110 is mounted to the toilet 510 through its base 138, in some cases, one or more components of the manipulation device 110 (e.g., one or more sets of arm mechanisms and grasping mechanisms) can be secured to the toilet 510 directly through one or more articulation joints (e.g., articulation joints 136a-b).

In some cases, the system 100 can be configured to conduct a pre-cleaning operation to cleanse the toilet 510 prior to use by a user and/or prepare the toilet 510 for use. As an example, the system 100 can be configured to operate the manipulation device 110 to cleanse one or more surfaces of the toilet 510 (e.g., the surface of the basin 512, a seating surface 532 atop the basin 512, or any other surface). As another example, the system 100 can be configured to operate the manipulation device 110 to place a cover or protector over the seating surface 532, such that the user does not directly contact the seating surface 532 during use of the toilet 510.

In some cases, the pre-cleaning operation can include one or more of the following steps.

A user can initiate the pre-cleaning operation by turning on or otherwise activating the system 100 (e.g., by manipulating a button or switch, vocalizing a command, or activating a motion sensor). In response, the manipulating device 110 unfolds its arm mechanisms 130a-b and 132a-b, such that they are extended away from the base 138. This can be performed, for example, by moving one or more of the arm mechanisms 130a-b and/or 132a-b with respect to the articulating joints 134a-b.

Figure 6A:
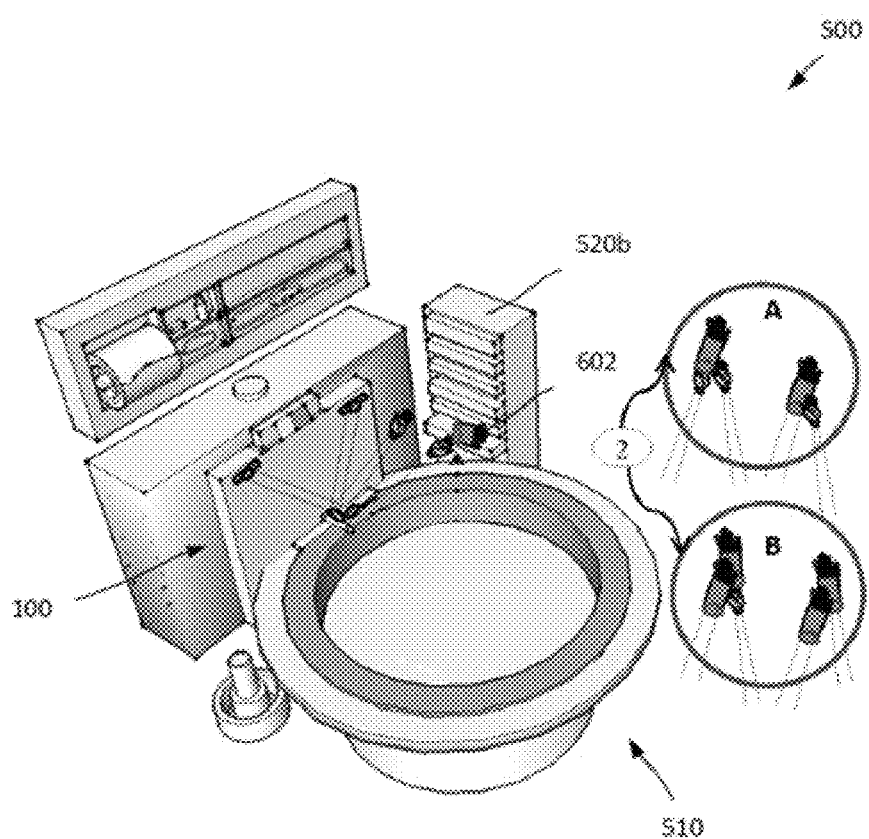
FIGS. 6A-6N are diagrams showing example operations of the sanitation system shown in FIG. 5.

As shown in FIG. 6A, the system 100 further guides the grasping mechanisms 140a-b towards a supply container 520b (e.g., by moving and/or reorienting one or more of its arm mechanisms and/or grasping mechanisms), and using the grasping mechanisms 140a-b, removes gloves 602 from the supply container 520b. The manipulating device 110 puts on the gloves 602 by securing each glove with one of the grasping mechanisms 140a-b (e.g., by pinching the glove using two or more finger mechanisms), and guiding the other grasping mechanism 140a-b into the interior of the glove (e.g., as shown in insets A and B).

Figure 6B:
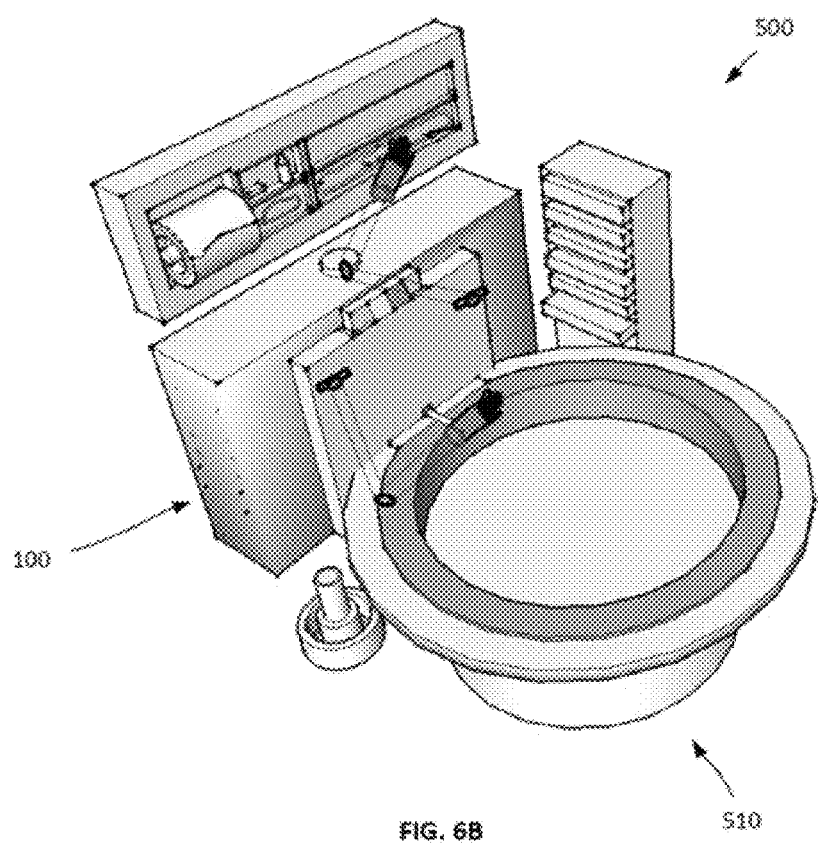

The system 100 prepares the toilet 510 use by lifting any coverings over the seating surface 532 (e.g., a toilet lid) by moving one of the grasping mechanisms (e.g., grasping mechanism 140a) towards the covering, grasping the covering (e.g., by pinching the covering using two or more finger mechanisms), and moving the grasping mechanism away from the seating surface 532 (e.g., by swinging the arm mechanism 132a upward with respect to the arm mechanism 130a, as shown in FIG. 6B).

Figure 6C:
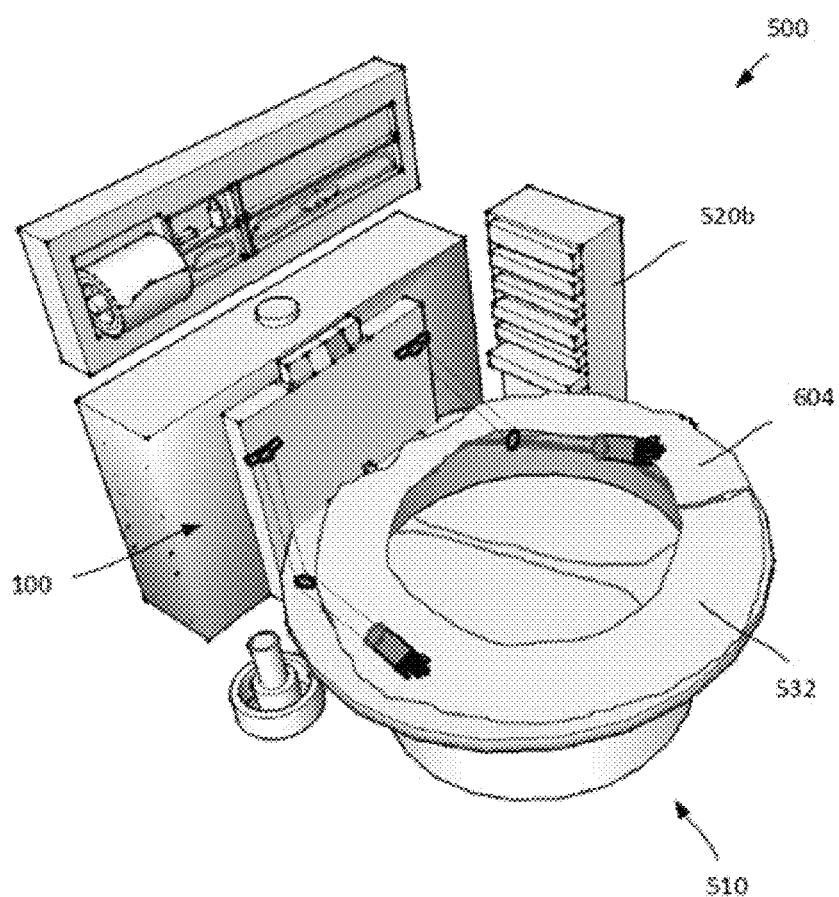

As shown in FIG. 6C, the system 100 further removes a seat cover 604 from the supply container 520b (e.g., by pinching the seat cover 604 using two or more finger mechanisms), unfolding the seat cover 604 (e.g., by grasping opposing sides of the seat cover 604 and moving the opposing sides away from each other), and positioning the seat cover 604 onto the seating surface 532 (e.g., by placing opposing sides of the seat cover 604 onto the front and back of the seating surface 532, respectively).

Further, the system 100 can ascertain whether one or more consumable items (e.g., soap, water, toilet tissue, cleaning agents, etc.) are in ample supply and available for use. In some cases, this can be determined using one or more sensors placed at the location of the consumable items (e.g., a proximity sensor, an optical sensor, a pressure sensor, etc.).

In some cases, the system 100 can be configured to cleanse the user's body after the user has finished using the toilet 510 (e.g., after the user has finished urinating and/or defecating). As an example, the system 100 can be configured to operate the manipulation device 110 to obtain one or more portions of toilet tissue, wipe the toilet tissue with against a part of the user's body (e.g., the user's posterior), and dispose of the used toilet tissue. As an example, the system 100 can be configured to operate the manipulation device 110 to cleanse a part of the user's body (e.g., the user's posterior) with one or more moistened wipes. As an example, the system 100 can be configured to apply water and/or a cleaning agent to a part of the user's body (e.g., the user's posterior), and dry the body part.

In some cases, the cleansing operation can include one or more of the following steps.

Figure 6D:
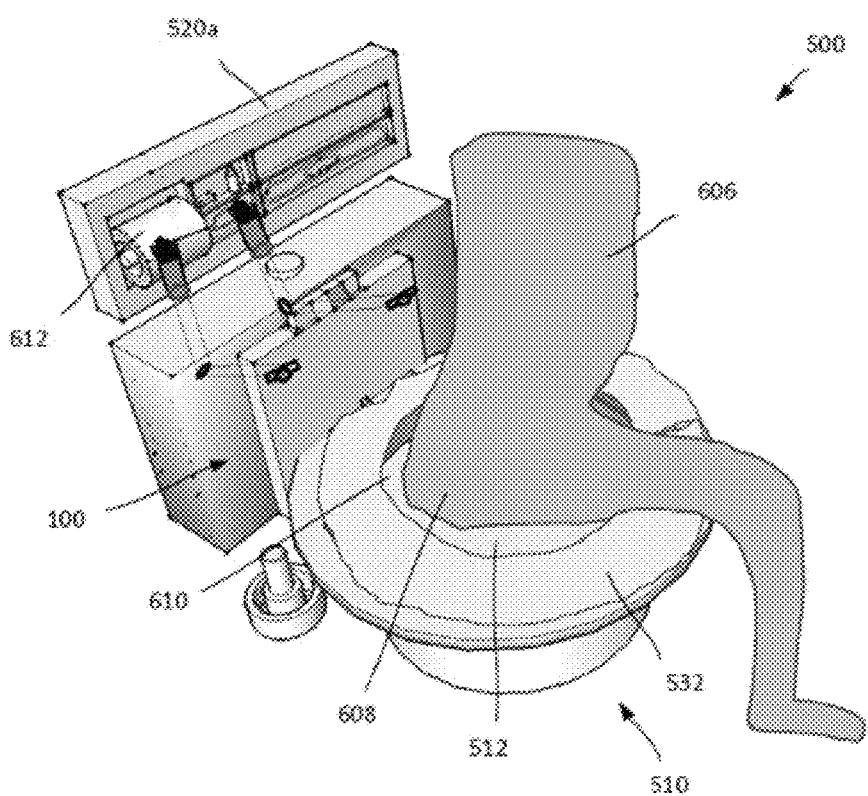

As shown in FIG. 6D, once the toilet 510 has been prepared for use, the user 606 positions himself above the basin 512 (e.g., by sitting onto the seating surface 532, such that his posterior 608 is positioned over the basin 512). In some cases, the user can seat himself such that an access space 610 is defined between the user 606 and the seating surface 532. This enables the system 100 to access the user's posterior 608 through the access space 610. In some cases, the access space 610 can be defined as a separate opening or channel that extends through the toilet 510.

The system 100 further guides a grasping mechanism (e.g., the grasping mechanism 140a) to a roll of toilet tissue 612 in the supply container 520a. The grasping mechanism secures an end of the toilet tissue 612 (e.g., by pinching the end of the toilet tissue 612 using two or more finger mechanisms), and folds the end of the toilet tissue 612 (e.g., by guiding the end of the toilet tissue 612 along the length of the toilet tissue 612, such that a portion of the toilet tissue 612 overlaps). The grasping mechanism then rotates the roll of toilet tissue 612 to dispense a length of toilet tissue 612 (e.g., by rolling the toilet tissue 612 around one or more of the finger elements 144a), and tears the toilet tissue 612 to separate the dispensed length of toilet tissue 612 from the roll. The grasping mechanism can also further fold the dispensed length of toilet tissue 612 one or more times. The grasping mechanism grasps the folded toilet tissue 612 between two more finger mechanisms, passes the folded toilet tissue 612 to another grasping mechanism (e.g., the grasping mechanism 140b), and repeats some or all of the steps above to prepare one or more additional folded portions of toilet tissue 612.

Figure 6E:
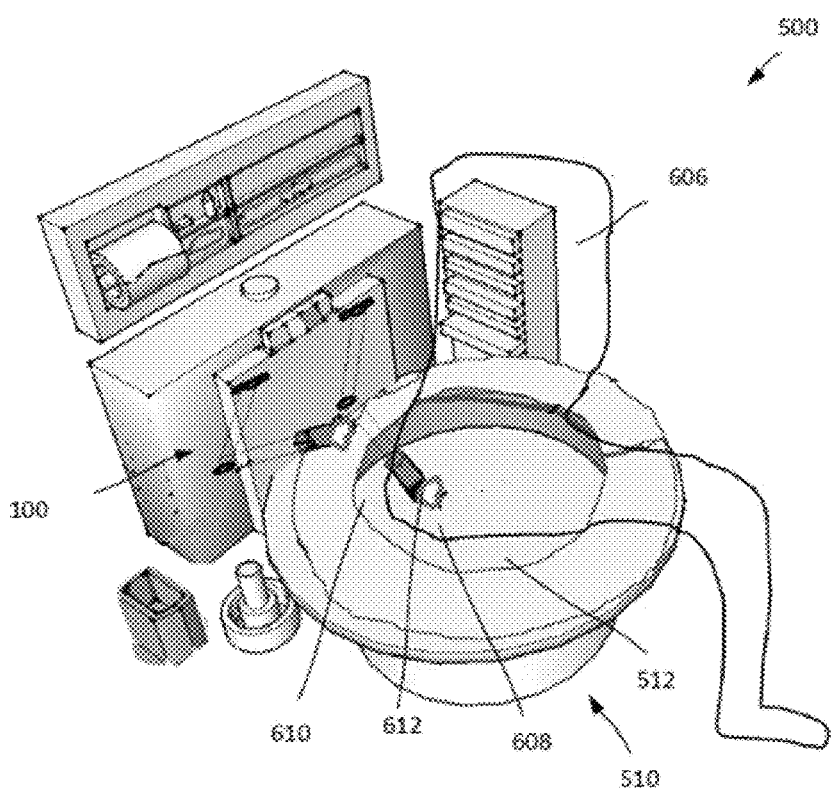

When the user is finished using the toilet 510 (e.g., when the user has finished urinating and/or defecating), the user can request that he be cleaned by the system 100 (e.g., by manipulating a button or switch, vocalizing a command, or activating a motion sensor). As shown in FIG. 6E, in response, the system 100 guides a grasping mechanism (e.g., the grasping mechanism 140b) through the access space 610 and towards the user's posterior 608. The system 100 subsequently guides the grasping mechanism upward, such that it contacts the user's posterior 608 with the folded toilet tissue 612. The system 100 then guides the grasping mechanism forwards and backwards one or more times, such that the folded toilet tissue 612 is wiped against the user's posterior 608. The system 100 then rotates the grasping mechanism such that the folded toilet tissue 612 is facing downwards toward the basin 512, and releases the folded toilet tissue 612 into the basin 512. The grasping mechanism obtains additional portion of folded toilet tissue 612 (e.g., from another grasping mechanism), and repeats some or all of the steps above to further wipe the user's posterior 608.

Figure 6F:
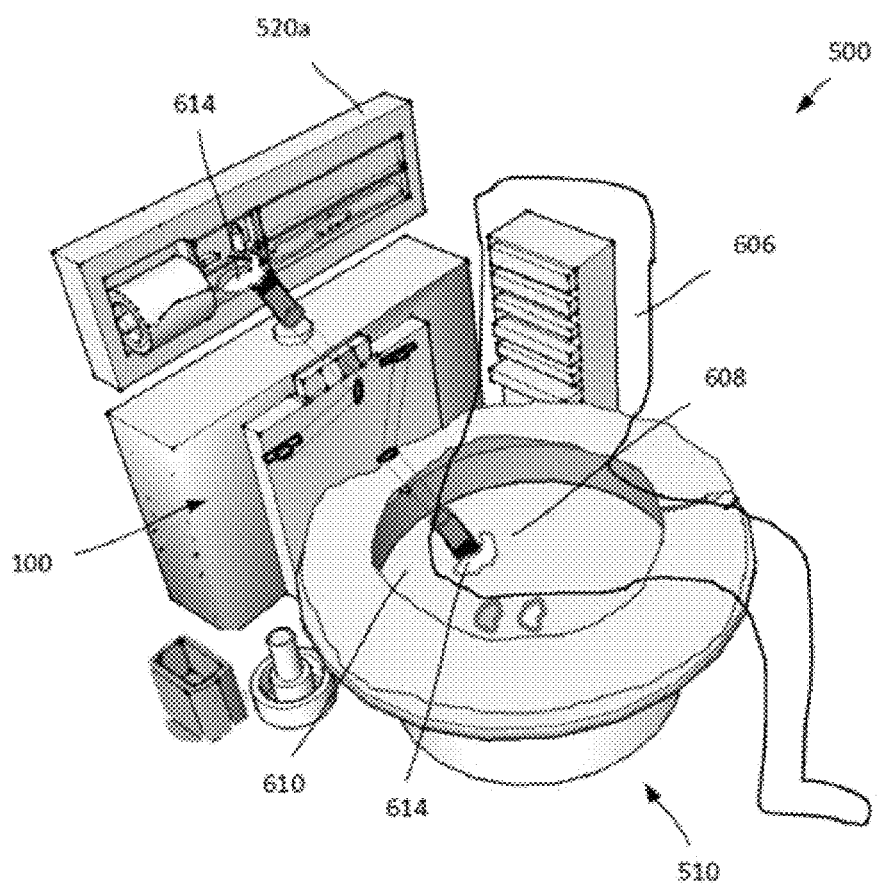

The system 100 can also cleanse the user's body using moistened wipes (e.g., a portion of cloth or paper that has been moistened with water and/or a cleaning agent). As shown in FIG. 6F, the system 100 guides a grasping mechanism (e.g., the grasping mechanism 140a) to a container of moistened wipes 614 in the supply container 520a. The grasping mechanism secures one of the moistened wipes 614 (e.g., by pinching the moistened wipe 614 using two or more finger mechanisms), and passes the moistened wipe 614 to another grasping mechanism (e.g., the grasping mechanism 140b). The grasping mechanism repeats some or all of the steps above to obtain one or more additional moistened wipes 614.

The system 100 guides a grasping mechanism (e.g., the grasping mechanism 140b) through the access space 610 and towards the user's posterior 608. The system 100 subsequently guides the grasping mechanism upward, such that it contacts the user's posterior 608 with the moistened wipe 614. The system 100 then guides the grasping mechanism forwards and backwards one or more times, such that the moistened wipe 614 is wiped against the user's posterior 608.

The system 100 can dispose of the used moistened wipe 614 by rotating the grasping mechanism such that the moistened wipe 614 is facing downwards toward the basin 512, and releasing the moistened wipe 614 into the basin 512. The grasping mechanism can subsequently obtain an additional moistened wipe 614 (e.g., from another grasping mechanism), and repeat some or all of the steps above to further wipe the user's posterior 608.

Figure 6G:
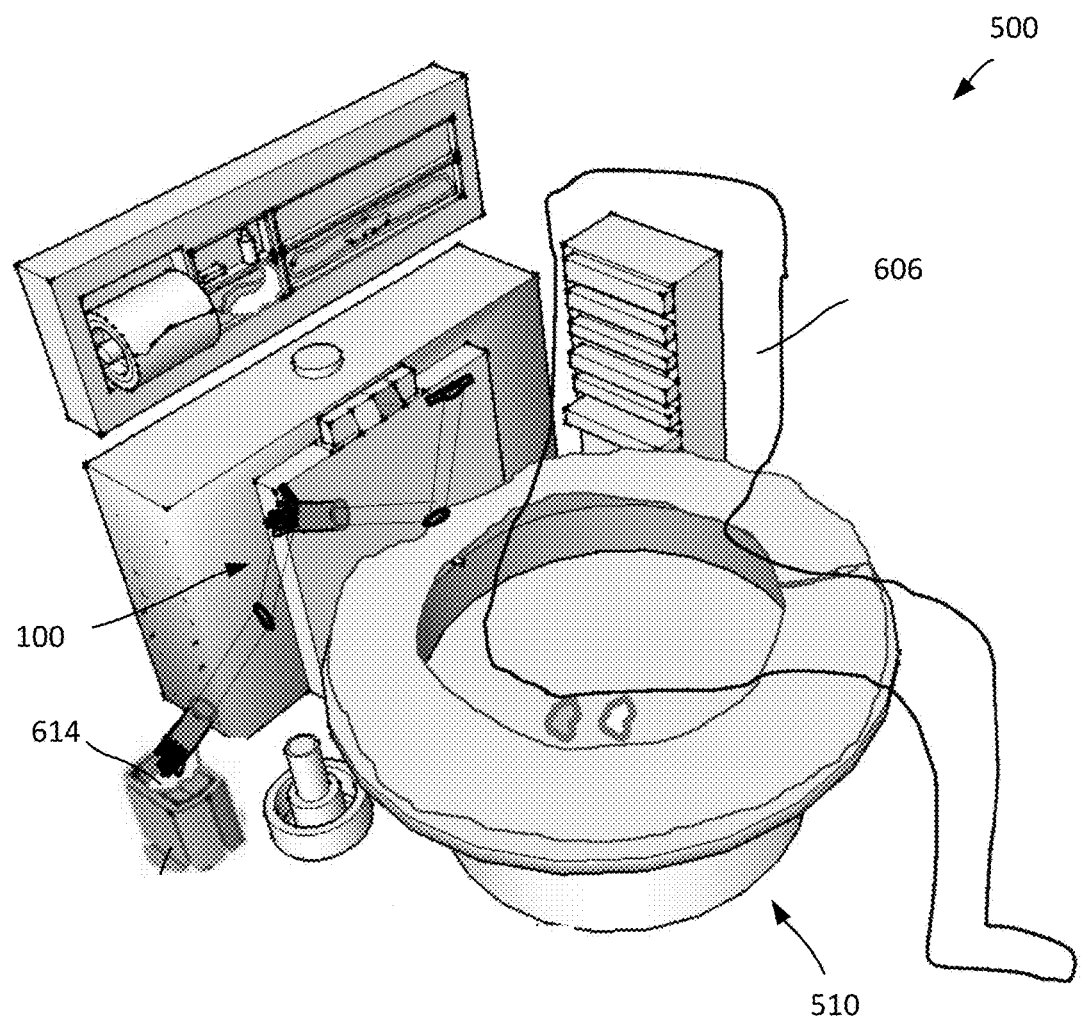

As shown in FIG. 6G, the system 100 can also dispose of the used moistened wipe 614 by removing the used moistened wipe 614 from underneath the user, and positioning the used moistened wipe 614 in or above a waste receptacle 616 (e.g., positioned nearby the toilet 510). The system 100 can rotate the grasping mechanism such that the moistened wipe 614 is facing downwards toward the waste receptacle 616, and release the moistened wipe 614 into the waste receptacle 616. Similarly, the grasping mechanism can subsequently obtain an additional moistened wipe 614 (e.g., from another grasping mechanism), and repeat some or all of the steps above to further wipe the user's posterior 608.

Figure 6H:
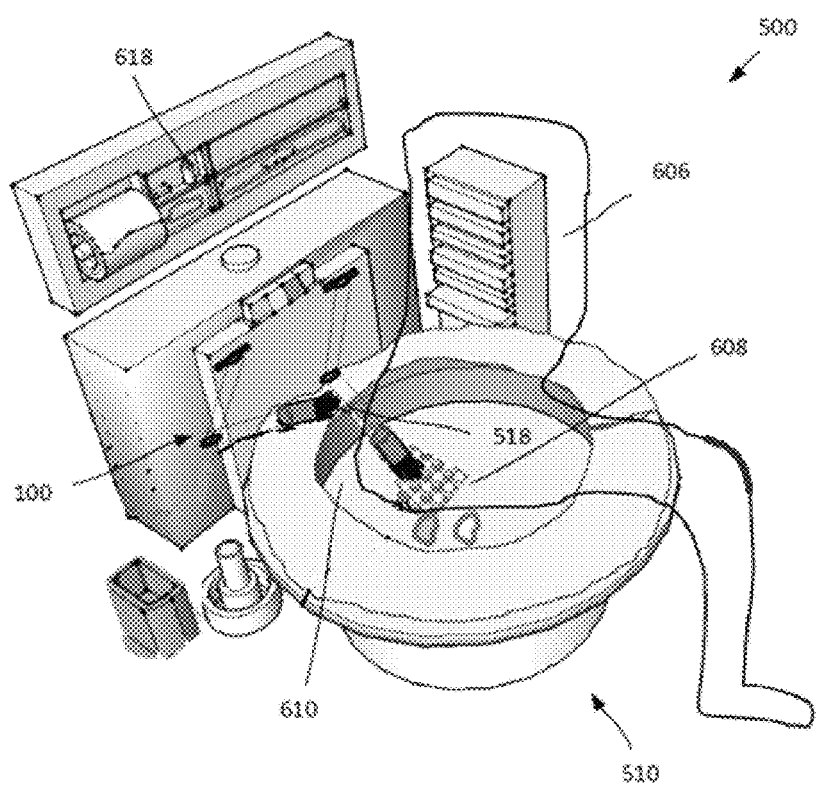
Figure 61:
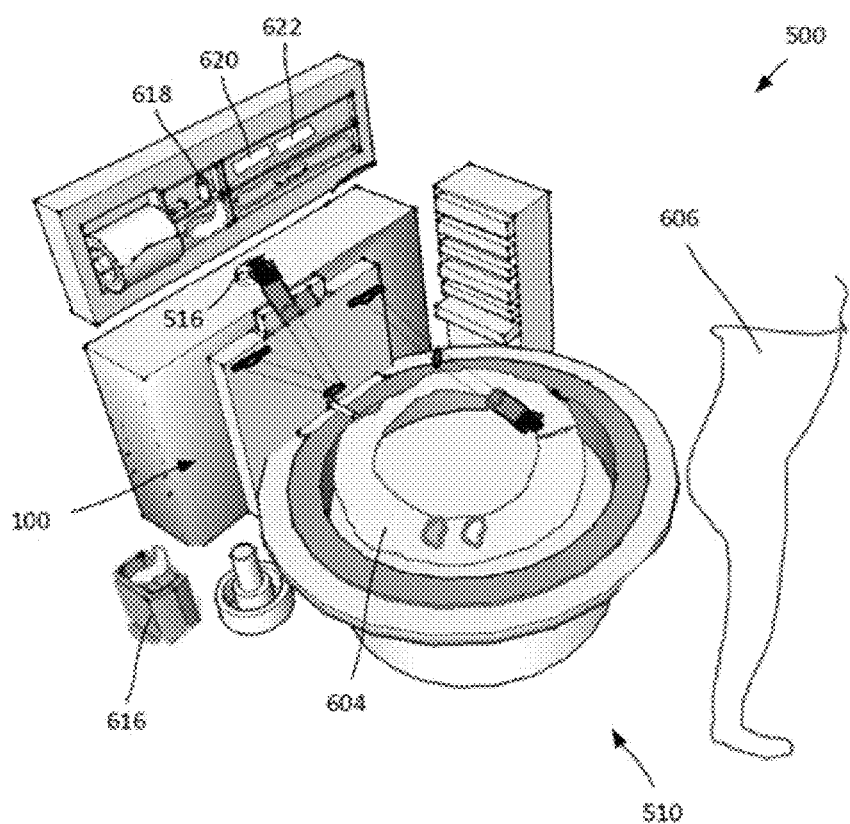

The system 100 can also cleanse the user's body by applying water and/or a cleaning agent to the user's posterior, and drying the user's posterior. As shown in FIG. 6H, the system 100 guides a grasping mechanism (e.g., the grasping mechanism 140b) to a soap dispenser 618, and obtains a portion of soap (e.g., by positioning the grasping mechanism 140b beneath a spout of the soap dispenser with each of the finger mechanisms aligned together, and pressing on a dispensing mechanism to release soap from the spout onto the grasping mechanism). The system 100 guides the grasping mechanism to the faucet 518, such that the dispensed soap is facing upward, and activates the faucet 518 (e.g., by pressing the faucet 518 inward with the grasping mechanism to actuate an internal water valve of the faucet 518). Accordingly, the grasping mechanism is moistened with a mixture of soap and water.

The system 100 guides the grasping mechanism (e.g., the grasping mechanism 140b) through the access space 610 and towards the user's posterior 608. The system 100 subsequently guides the grasping mechanism upward, such that it contacts the user's posterior 608. The system 100 then guides the grasping mechanism forwards and backwards one or more times, such that the soap is wiped against the user's posterior 608. The grasping mechanism can subsequently repeat some or all of the steps above to further cleanse the user's posterior 608 with soap.

The system 100 dries the user's posterior 608 by wiping the user's posterior 608 with one or more portions of toilet tissue. For example, the user can perform some or all of the steps described with respect to FIGS. 6D and 6E to dry the user's posterior 608 with toilet tissue.

As shown in FIG. 6I, once the user has been cleaned, the system 100 can activate the flushing mechanisms 516 (e.g., by guiding a grasping mechanism to the flushing mechanism 516 and pressing a button), thereby disposing the contents of the basin 512. The system 100 can further notify the user 606 that the cleaning process is complete (e.g., by emitting an auditory signal or message and/or displaying a visual signal or message).

In some cases, the user can unseat himself upon completion of the cleaning process. In some cases, the user can remain seated, and request that one or more of the cleaning steps be repeated (e.g., by manipulating a button or switch, vocalizing a command, or activating a motion sensor).

After the user has finished using the toilet 510, the system 100 can clean the toilet 510 and/or prepare it for future use. For example, the system 100 can be configured to operate the manipulation device 110 to dispose of seat coverings on the seating surface 532. As another example, the system 100 can be configured to operate the manipulation device 110 to cleanse one or more surfaces of the toilet 510 (e.g., the surface of the basin 512, the seating surface 532, or any other surface).

In some cases, the post-use operation can include one or more of the following steps.

As shown in FIG. 6I, the manipulating device 110 places the seat cover 604 into the basin 512 (e.g., by pushing a grasping mechanism against the seat cover 604 such that the seat cover 604 falls into the basin 512, or by grasping the seat cover 604 with a grasping mechanism and releasing the seat cover 604 into the basin 512).

The manipulating device 110 cleanses the toilet 510 by guiding a grasping mechanism (e.g., the grasping mechanism 140b) to a cleaning sponge or tissue 620, grasping the cleaning sponge or tissue 620 (e.g., by pinching or gripping the cleaning sponge or tissue 620 using two or more finger mechanisms), and guiding the cleaning sponge or tissue 620 to the soap dispenser 618. The manipulating device 110 applies a portion of soap to the cleaning sponge or tissue 620 (e.g., by positioning the cleaning sponge or tissue beneath a spout of the soap dispenser, and pressing on a dispensing mechanism to release soap from the spout onto the cleaning sponge or tissue 620). The system 100 guides the grasping mechanism to the faucet 518, and activates the faucet 518 (e.g., by pressing the faucet 518 inward with the grasping mechanism to actuate an internal water valve of the faucet 518). Accordingly, the cleaning sponge or tissue 620 is moistened with a mixture of soap and water.

The system 100 guides the grasping mechanism to the seating surface 532, rotates the grasping mechanism such that the cleaning sponge or tissue 620 is facing downwards toward the seating surface 532. The system 100 then guides the grasping mechanism forwards and backwards and/or in a rotating motion one or more times, such that the soap is wiped against the seating surface 532. The grasping mechanism can subsequently repeat some or all of the steps above to further cleanse the seating surface 532.

The system 100 can dispose of the used cleaning sponge or tissue 620 by re-positioning the cleaning sponge or tissue 620 over the basin 512, rotating the grasping mechanism such that the cleaning sponge or tissue 620 is facing downwards toward the basin 512, and releasing the cleaning sponge or tissue 620 into the basin 512.

In some cases, the system 100 also can dispose of the used cleaning sponge or tissue 620 by positioning the cleaning sponge or tissue 620 in or above a waste receptacle 616. The system 100 can rotate the grasping mechanism such that the cleaning sponge or tissue 620 is facing downwards toward the waste receptacle 616, and release the cleaning sponge or tissue 620 into the waste receptacle 616.

In some instances, the system 100 also can wash the used cleaning sponge or tissue 620, such that it can be reused. The system 100 can position the cleaning sponge or tissue 620 close to the faucet 518, activate the faucet 518, and squeeze the cleaning sponge or tissue 620 (e.g., by repeatedly tightly grasping and ungrasping the cleaning sponge or tissue 620 with one or more finger mechanisms). Accordingly, the cleaning sponge or tissue 620 is rinsed by the water. The system 100 can subsequently replace the cleaning sponge or tissue 620 in its original storage location.

The system 100 subsequently activates the flushing mechanisms 516 (e.g., by guiding a grasping mechanism to the flushing mechanism 516 and pressing a button), thereby disposing the contents of the basin 512.

Further, the system 100 can clean the basin 512. The system 100 guides a grasping mechanism to a container of cleaning solution 622 (e.g., bleach or soap), and transfers it to the basin 512 (e.g., by positioning the container of cleaning solution 622 above the basin 512 and upending the container of cleaning solution 622 for a period of time). The system 100 replaces the container of cleaning solution 622 to its original storage location.

Figure 6K:
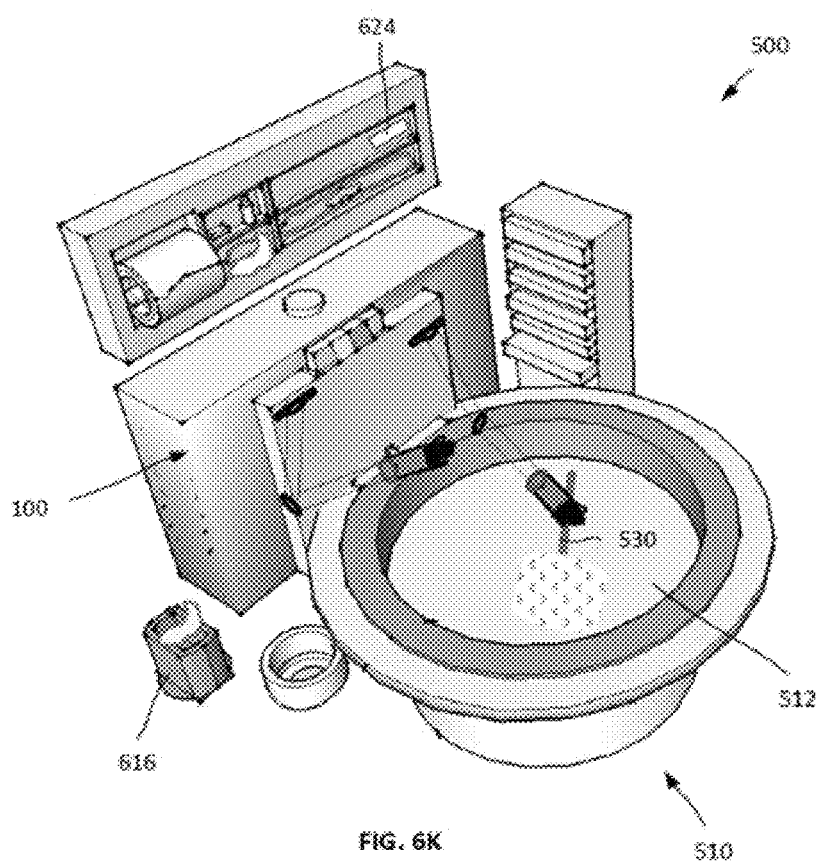

Further, as shown in FIG. 6J, the system 100 guides a grasping mechanism (e.g., the grasping mechanism 140a) to the cleaning tool 530, and grasps the cleaning tool 530 (e.g., by pinching or gripping the cleaning tool 530 using two or more finger mechanisms). As shown in FIG. 6K, the system 100 guides the cleaning tool 530 to the interior of the basin 512, and moves the cleaning tool 530 in a rotating motion one or more times, such that the cleaning tool 530 is scrubbed against the interior of the basin 512.

After scrubbing the basin 512, the system 100 positions the cleaning tool 530 close to the faucet 518, and activates the faucet 518. Accordingly, the cleaning tool 530 is rinsed by the water. The system 100 can subsequently tap the cleaning tool 530 against an upper portion of the basin 512 (e.g., to remove remaining amounts of water from the cleaning tool 530), and replace the cleaning tool 530 in its original storage location.

Further, the system 100 can dry the seating surface 532. The system 100 guides a grasping mechanism to towel dispenser 624 (e.g., a paper towel dispenser), and grasps and removes a towel from the towel dispenser 624 (e.g., by pinching a towel using two or more finger mechanisms). The system 100 guides the grasping mechanism to the seating surface 532, rotates the grasping mechanism such that the towel is facing downwards toward the seating surface 532. The system 100 then guides the grasping mechanism forwards and backwards and/or in a rotating motion one or more times, such that the towel is wiped against the seating surface 532. If the towel can be safely flushed in a toilet, the towel can be disposed of in the basin 512 (e.g., in a similar manner as disposing toilet tissue and/or moistened wipes, as described above). Otherwise, the towel can be disposed of in the waste receptacle 616 (e.g., in a similar manner as described above). The grasping mechanism can subsequently repeat some or all of the steps above to further dry the seating surface 532.

Figure 6L:
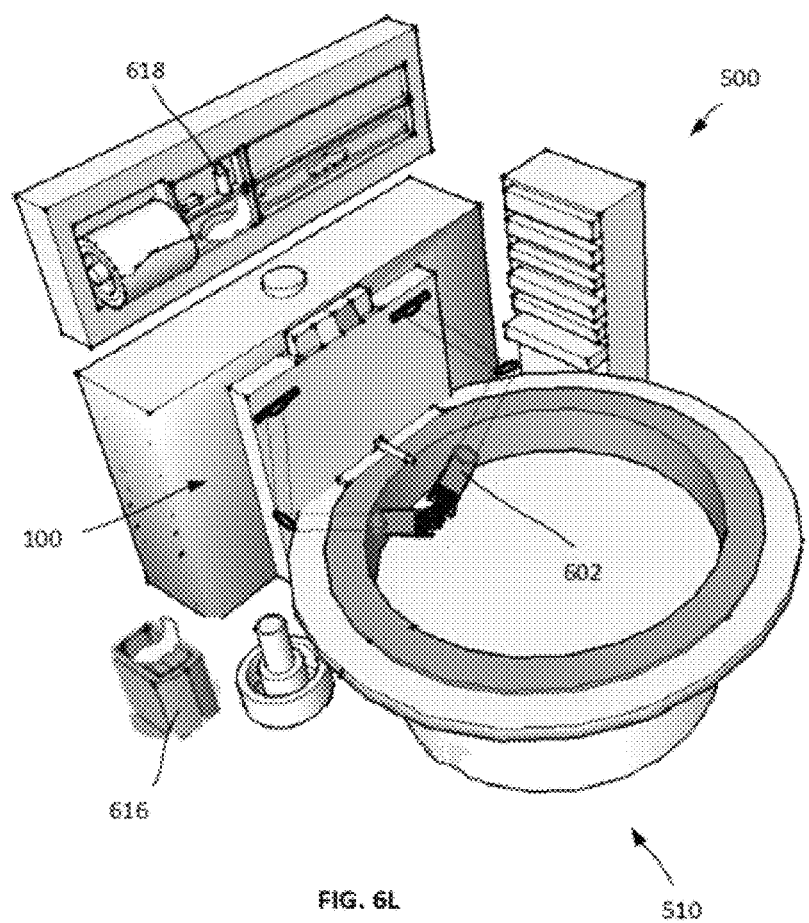

As shown in FIG. 6L, the system 100 can dispose of the gloves 602 by removing the gloves 602 from the grasping mechanisms (e.g., by pinching the glove covering one grasping mechanism using two or more finger mechanisms of another grasping mechanism), and releasing the gloves 602 into the waste receptacle 616.

The system 100 also can cleanse itself, such that it remains clean and sanitary. For example, the system 100 can be configured to operate the manipulation device 110 to cleanse itself using water from the faucet 518 and/or a cleaning agent (e.g., soap, disinfectant, bleach, etc.)

In some cases, the self-cleaning operation can include one or more of the following steps.

Figure 6M:
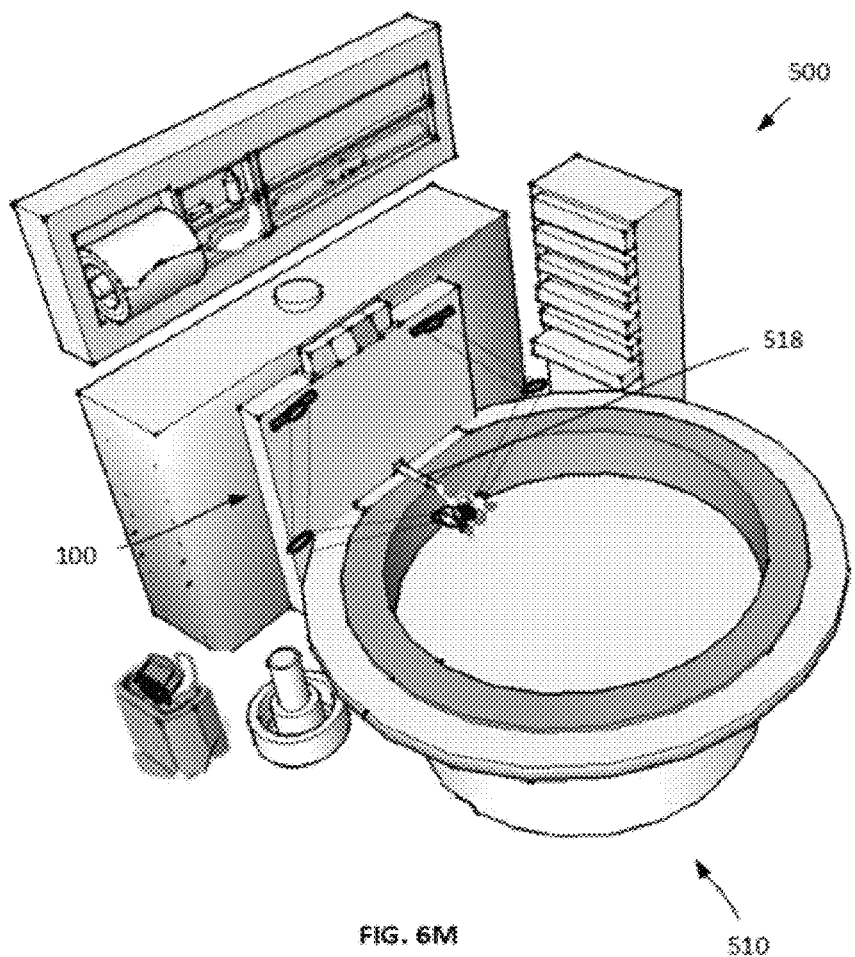

The system 100 guides a grasping mechanism (e.g., the grasping mechanism 140b) to the soap dispenser 618, and obtains a portion of soap (e.g., by positioning the grasping mechanism 140b beneath a spout of the soap dispenser with each of the finger mechanisms aligned together, and pressing on a dispensing mechanism to release soap from the spout onto the grasping mechanism). As shown in FIG. 6M, the system 100 guides each of the grasping mechanisms to the faucet 518, such that the dispensed soap is facing upward, and activates the faucet 518 (e.g., by pressing the faucet 518 inward with the grasping mechanism to actuate an internal water valve of the faucet 518). Accordingly, the grasping mechanism is moistened with a mixture of soap and water. The system 100 moves the grasping mechanisms against each other (e.g., in a rotating motion), such that the grasping mechanisms are scrubbed by one another. In some cases, the system 100 can align the finger mechanisms of one grasping mechanism with corresponding finger mechanisms of another grasping mechanism (e.g., so that each finger mechanism contacts a corresponding finger mechanism), and impart a rotating motion in one or more of the grasping mechanisms, such that each of the finger mechanisms is scrubbed. In some cases, the system 100 can articulate one or more of the finger mechanisms (e.g., curling and uncurling one or more finger mechanisms) and/or move one or more of the grasping mechanisms in a manner such that each of the surfaces of the grasping mechanism is scrubbed (e.g., back surfaces, front surfaces, side surfaces, top surfaces, bottom surfaces, and so forth). The system 100 can further rinse the grasping mechanisms (e.g., to remove the soap) by positioning the grasping mechanisms under the faucet 518 while it is dispensing water for a period of time. The grasping mechanisms can subsequently repeat some or all of the steps above to further cleanse the system 100.

Figure 6N:
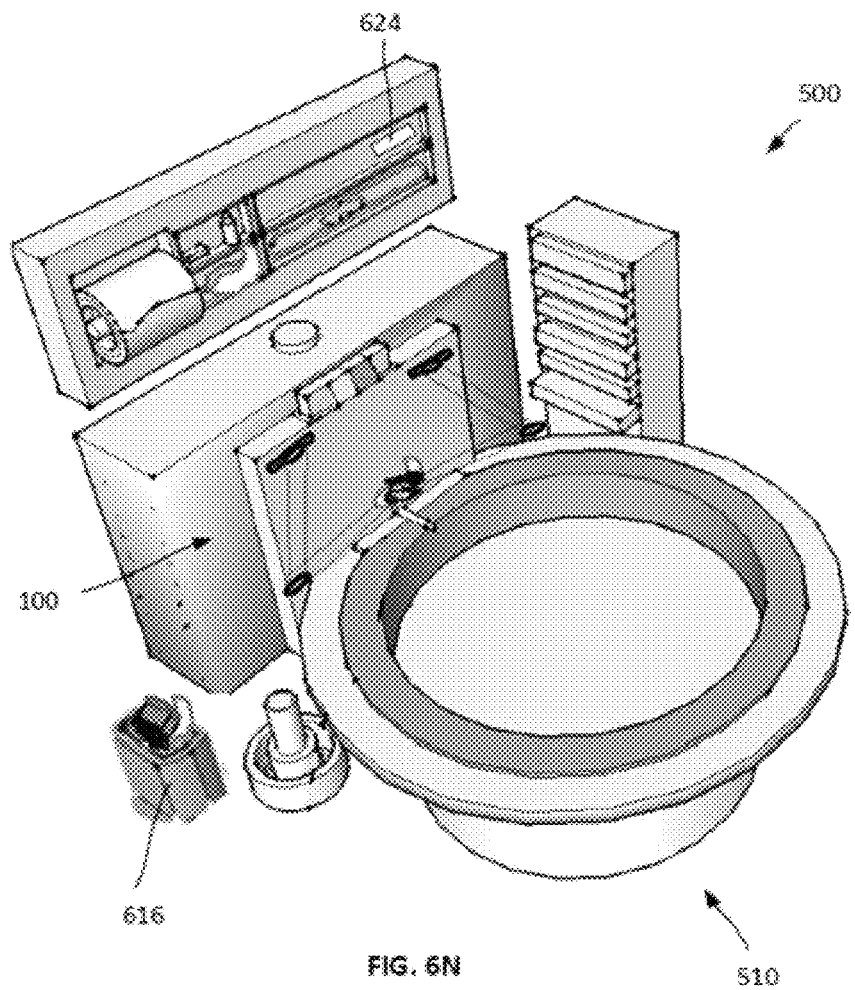

The system 100 dries itself by guiding a grasping mechanism to towel dispenser 624 (e.g., a paper towel dispenser), and grasping and removing a towel from the towel dispenser 624 (e.g., by pinching the cleaning tool 530 using two or more finger mechanisms). As shown in FIG. 6N, the system 100 rubs the grasping mechanisms against the towel, thereby drying the grasping mechanisms. The towel can be disposed of in the waste receptacle 616 (e.g., in a similar manner as disposing moistened wipes, as described above). The grasping mechanisms can subsequently repeat some or all of the steps above to further dry the system 100.

The system 100 also can use a towel to dry other surfaces of the system 500 (e.g., the seating surface 532, the faucet 518, the soap dispenser 618, or another surface of the system 500), and dispose of the towel in the waste receptacle 616.

The system 100 also can replace the covering over the seating surface 532 (e.g., the toilet lid) by moving one of the grasping mechanisms (e.g., grasping mechanism 140a) towards the covering, grasping the covering (e.g., by pinching the covering using two or more finger mechanisms), and moving the grasping mechanism towards from the seating surface 532 (e.g., by swinging the arm mechanism 132a downward with respect to the arm mechanism 130a).

Upon completion, the system 100 can return the manipulating device 110 to its original position and/or orientation.

Although examples of toilet-related applications are described here, these are merely illustrative examples. In practice, the system 100 can be used in any environment to mimic the functionality of human arms and hands. For example, in some cases, the system 100 can be used in conjunction with a sink to facilitate the washing of a user's hands or other items such as clothing, a urinal to facilitate use of the urinal, a shower to facilitate the washing a user's body, and so forth.

Figure 7A:
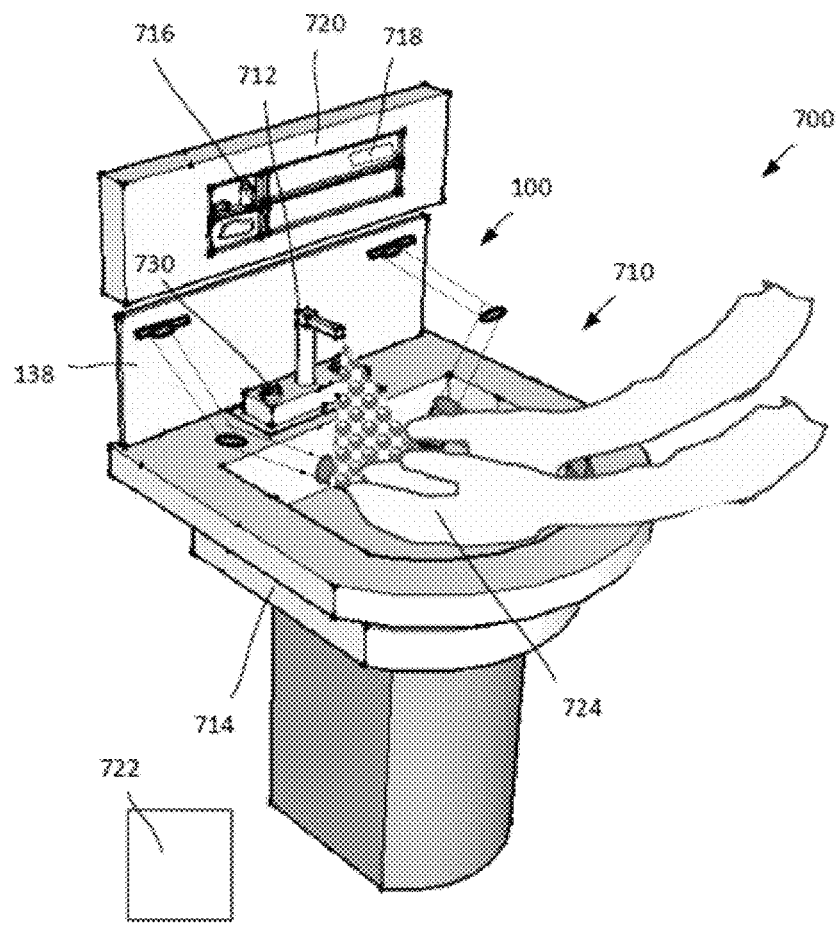
FIGS. 7A and 7B are diagrams of an example cleaning system for washing parts of a user's body.

As an example, FIG. 7A shows a cleaning system 700. Implementations of the cleaning system 700 can be used to wash parts of a user's body (e.g., hands, arms, face, etc.) and/or other objects (e.g., articles of clothing, towels, etc.) The system 700 includes a sink 710 and a supply container 720. The system 700 also includes a system 100 for mimicking arm and hand movement (e.g., as shown and described with respect to FIGS. 1 and 2).

The sink 710 is a plumbing fixture that dispenses and collects water, and facilities activities that use water (e.g., cleaning and washing). The sink 710 includes a faucet 712 that dispenses water, and a basin 714 that collects water. In an example implementation, a user can place a part of his body and/or an object under the faucet 712, such that water dispensed by the faucet 712 flows over his body and/or the object. Water is collected by the basin 714, and removed from the sink 710 (e.g., through a tube, pipe, or other conduit in fluid communication with a sewage or septic system).

The supply container 720 contains objects or consumable items that facilitate use and/or maintenance of the system 700. For example, the supply container 720 can contain towels, cleaning agents (e.g., soap, disinfectants, bleach, cleaning solutions, cleaning powders, etc.), gloves, and so forth.

The system 700 also includes a system 100 for mimicking arm and hand movement. As described above, the system 100 can be similar to that shown and described with respect to FIGS. 1 and 2. For example, as shown in FIG. 7A, the system 100 can include a first set of arm mechanisms 130a and 132a, grasping mechanism 140a having fingers mechanisms 144a, and articulating joints 134a, 136a, 142a, and 146a (referencing FIG. 1). In some cases, these two sets of components can mimic the functionality of two human arms and two human hands.

The system 100 can be mounted to the sink 710 or in proximity to the sink 710, such that the system 100 can access one or more of the components of the system 700. For example, as shown in FIG. 7A, the system 100 can be mounted above the sink 710.

Although an example position for the system 100 is shown, this is merely an illustrative example. In practice, the system 100 can be secured and/or positioned at different locations, depending on the implementation.

Further, although FIG. 7A shows an example in which the manipulation device 110 is mounted through its base 138, in some cases, one or more components of the manipulation device 110 (e.g., one or more sets of arm mechanisms and grasping mechanisms) can be secured directly through one or more articulation joints (e.g., articulation joints 136a-b).

In some cases, the system 100 can be configured to assist a user in washing his hands. As an example, the system 100 can be configured to operate the manipulation device 110 to dispense soap onto a user's hands, scrub the user's hands, rinse the user's hands, and dry the user's hands.

In some cases, the washing operation can include one or more of the following steps.

A user can initiate the washing operation by turning on or otherwise activating the system 100 (e.g., by manipulating a button or switch, vocalizing a command, or activating a motion sensor). In response, the manipulating device 110 unfolds its arm mechanisms 130a-b and 132a-b, such that they are extended away from the base 138. This can be performed, for example, by moving one or more of the arm mechanisms 130a-b and/or 132a-b with respect to the articulating joints 134a-b.

The system 100 guides a grasping mechanism (e.g., the grasping mechanism 140b) to a soap dispenser 716, and obtains a portion of soap (e.g., by positioning the grasping mechanism 140b beneath a spout of the soap dispenser with each of the finger mechanisms aligned together, and pressing on a dispensing mechanism to release soap from the spout onto the grasping mechanism). The system 100 guides each of the grasping mechanisms to the faucet 712, such that the dispensed soap is facing upward, and activates the faucet 712 (e.g., rotating a water release valve 730 with another grasping mechanism, such as the grasping mechanism 140a). Accordingly, the grasping mechanism is moistened with a mixture of soap and water. The system 100 positions the grasping mechanisms against a user's hands 724, and moves the grasping mechanisms against the user's hands 724 (e.g., in a rotating motion), such that the user's hands 724 are scrubbed by the grasping mechanisms. In some cases, the system 100 can align the finger mechanisms of a grasping mechanism with corresponding fingers of the user's hand 724 (e.g., so that each finger mechanism contacts a corresponding finger of the user's hand 724), and impart a rotating motion in the grasping mechanism, such that each of the user's fingers is scrubbed. In some cases, the system 100 can articulate one or more of the finger mechanisms (e.g., curling and uncurling one or more finger mechanisms) and/or move one or more of the grasping mechanisms in a manner such that each of the surfaces of the user's hands 724 is scrubbed (e.g., back surfaces, front surfaces, side surfaces, top surfaces, bottom surfaces, and so forth). The system 100 can further rinse the grasping mechanisms (e.g., to remove the soap) by positioning the grasping mechanisms under the faucet 712 while it is dispensing water for a period of time. The system 100 can further rinse the user's hands 724 by grasping the user's hands 724, and positioning the user's hands 724 under the faucet 712 while it is dispensing water for a period of time. The grasping mechanisms can subsequently repeat some or all of the steps above to further wash the user's hands 724.

The system 100 dries the user's hands by guiding a grasping mechanism to towel dispenser 718 (e.g., a paper towel dispenser), and grasping and removing a towel from the towel dispenser 718 (e.g., by pinching a towel using two or more finger mechanisms). The system 100 rubs the towel against the user's hands 724 using the grasping mechanisms, thereby drying the user's hands 724. The towel can be disposed of in a waste receptacle 722 by positioning the used towel in or above a waste receptacle 722. The system 100 can rotate the grasping mechanism such that the towel is facing downwards toward the waste receptacle 722, and release the towel into the waste receptacle 722. The grasping mechanisms can subsequently repeat some or all of the steps above to further dry the user's hands 724.

The system 100 can further notify the user that the cleaning process is complete (e.g., by emitting an auditory signal or message and/or displaying a visual signal or message).

In some cases, the system 100 can be configured to clean the sink 710. As an example, the system 100 can be configured to operate the manipulation device 110 to scrub the sink 710 with water and/or a cleaning agent (e.g., soap) and rinse the sink 710.

In some cases, the cleaning operation can include one or more of the following steps.

The system 100 guides a grasping mechanism to towel dispenser 718 (e.g., a paper towel dispenser), and grasps and removes a towel from the towel dispenser 718 (e.g., by pinching a towel using two or more finger mechanisms). The system 100 dispenses a portion of soap onto the towel (e.g., by positioning the grasping mechanism such that the towel is positioned beneath a spout of the soap dispenser, and pressing on a dispensing mechanism to release soap from the spout onto the towel). The system 100 guides the grasping mechanism with the towel to the faucet 712, and activates the faucet 712 (e.g., rotating a water release valve 730 with another grasping mechanism, such as the grasping mechanism 140*a*). Accordingly, the grasping mechanism is moistened with a mixture of soap and water. The system 100 guides the grasping mechanism with the towel to the sink 710 (e.g., the faucet 712, the basin 714, or any other surface of the sink 710), rotates the grasping mechanism such that the towel is facing towards the surface of the sink 710. The system 100 then guides the grasping mechanism forwards and backwards and/or in a rotating motion one or more times, such that the towel is wiped against the surface of the sink 710. The grasping mechanism can subsequently repeat some or all of the steps above to further cleanse the sink 710.

Further, the system 100 can dry the sink 710. The system 100 guides a grasping mechanism to towel dispenser 718 (e.g., a paper towel dispenser), and grasps and removes a towel from the towel dispenser 718 (e.g., by pinching a towel using two or more finger mechanisms). The system 100 guides the grasping mechanism to the sink 710, rotates the grasping mechanism such that the towel is facing downwards toward the sink 710. The system 100 then guides the grasping mechanism forwards and backwards and/or in a rotating motion one or more times, such that the towel is wiped against the sink 710. The towel can be disposed of the waste receptacle 722 (e.g., in a similar manner as described above). The grasping mechanism can subsequently repeat some or all of the steps above to further dry the sink 710.

Upon completion, the system 100 can return the manipulating device 110 to its original position and/or orientation.

In some cases, the system 100 can be configured to assist a user in washing items (e.g., articles of clothing, towels, etc.). As an example, the system 100 can be configured to operate the manipulation device 110 to dispense soap or detergent onto an item, scrub the item, and rinse the item.

In some cases, the washing operation can include one or more of the following steps.

A user can initiate the washing operation by placing an item 728 (e.g., an article of clothing, a towel, etc.) into the basin 714, and turning on or otherwise activating the system 100 (e.g., by manipulating a button or switch, vocalizing a command, or activating a motion sensor). In response, the manipulating device 110 unfolds its arm mechanisms 130*a*-*b* and 132*a*-*b*, such that they are extended away from the base 138. This can be performed, for example, by moving one or more of the arm mechanisms 130*a*-*b* and/or 132*a*-*b* with respect to the articulating joints 134*a*-*b*.

The system 100 guides a grasping mechanism (e.g., the grasping mechanism 140*b*) to a soap dispenser 716, and obtains a portion of soap. For example, the system 100 can position the grasping mechanism 140*b* beneath a spout of the soap dispenser with each of the finger mechanisms aligned together, press on a dispensing mechanism to release soap from the spout onto the grasping mechanism, guide the grasping mechanism 140*b* towards the item such that it contacts the items 728 and transfers the soap to the item 728. As another example, the system 100 can guide a grasping mechanism to a container of detergent 726, and transfers it to the basin 714 (e.g., by positioning the container of detergent 726 above the basin 714 and upending the container of detergent 726 for a period of time). The system 100 replaces the container of detergent 726 to its original storage location. The system 100 spreads the soap and/or detergent onto the item 728 by rubbing the grasping mechanisms against the item 728 in a forwards and backwards and/or rotating motion. In some cases, one grasping mechanism can grasp a portion of the item 728 such that it is relatively secure, and another grasping mechanism can rub the item 728 (e.g., to scrub the item 728 with soap and/or detergent). In some cases, the system 100 can wait for a period of time (e.g., five minutes, 10 minutes, or some other period of time) to allow the soap and/or detergent to soak on or within the item 728. The grasping mechanisms can subsequently repeat some or all of the steps above to further spread soap and/or detergent into the item 728.

Figure 7B:
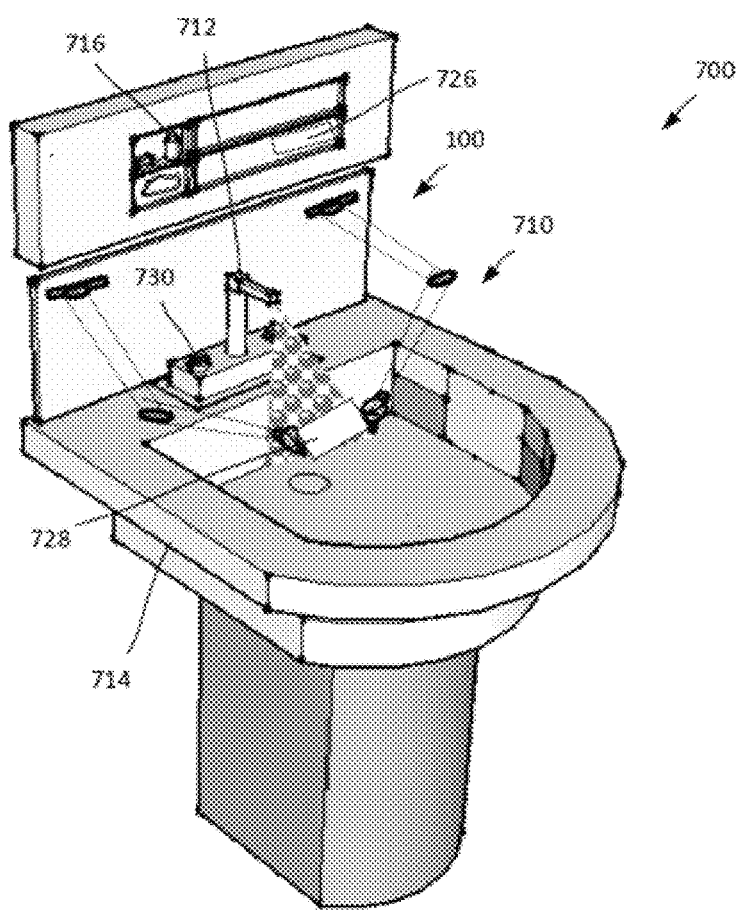

To rinse the item 728, the system 100 guides a grasping mechanism to the faucet 712 and activates it (e.g., rotating a water release valve 730). As shown in FIG. 7B, the system 100 grasps the item 728 with the grasping mechanisms and positions the item under the faucet 712, such that the item 728 is rinsed with water. In some cases, one grasping mechanism can grasp a portion of the item 728 such that it is relatively secure, and another grasping mechanism can rub the item 728 (e.g., to scrub the item clean). In some cases, the grasping mechanisms can press the item 728 (e.g., by applying pressure to one or more surfaces of the item, such that excess water is removed from the item 728. The grasping mechanisms can subsequently repeat some or all of the steps above to further rinse the item 728.

Once the item 728 has been cleaned, the system 100 can remove the cleaned item 728 from the basin 714 (e.g., by placing the item 728 in a container or on a hanger). The system 100 can further notify the user that the cleaning process is complete (e.g., by emitting an auditory signal or message and/or displaying a visual signal or message). Further the system 100 can clean itself and/or the sink 710 (e.g., in a similar manner as described above).

The system 100 can also dispose of the gloves on the grasping mechanisms (e.g., in a similar manner as described above) and/or clean itself (e.g., clean the grasping mechanisms using water and/or a cleaning agent in a similar manner as described above).

Upon completion, the system 100 can return the manipulating device 110 to its original position and/or orientation.

Another example sanitation system 800 for storing or disposing of human waste. The system 800 includes a urinal 810 and a supply container 820. The system 800 also includes a system 100 for mimicking arm and hand movement (e.g., as shown and described with respect to FIGS. 1 and 2).

The urinal 810 is a sanitation fixture used for the storing or disposal of human waste (e.g., urine) that can be used while a user is in an upright or standing position. The urinal 810 includes a basin 812 for collecting human waste.

The supply container 820 contains objects or consumable items that facilitate use and/or maintenance of the system 800. For example, the supply container 820 can contain towels, cleaning agents (e.g., soap, disinfectants, bleach, cleaning solutions, cleaning powders, etc.), gloves, and so forth.

Figure 8A:
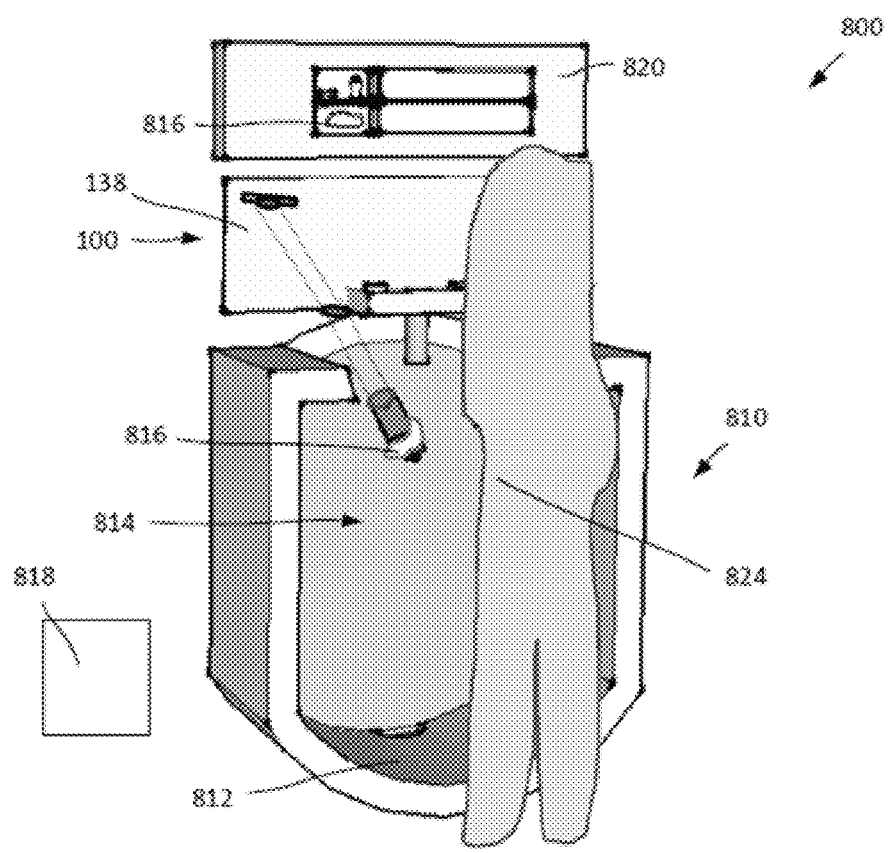
FIGS. 8A-8B are diagrams of another example sanitation system.

The system 800 also includes a system 100 for mimicking arm and hand movement. As described above, the system 100 can be similar to that shown and described with respect to FIGS. 1 and 2. For example, as shown in FIG. 8A, the system 100 can include a first set of arm mechanisms 130a and 132a, grasping mechanism 140a having fingers mechanisms 144a, and articulating joints 134a, 136a, 142a, and 146a (referencing FIG. 1). In some cases, these two sets of components can mimic the functionality of two human arms and two human hands.

The system 100 can be mounted to the urinal 810 or in proximity to the urinal 810, such that the system 100 can access one or more of the components of the system 800. For example, as shown in FIG. 8A, the system 100 can be mounted above the urinal 810.

Although an example position for the system 100 is shown, this is merely an illustrative example. In practice, the system 100 can be secured and/or positioned at different locations, depending on the implementation.

Further, although FIG. 8A shows an example in which the manipulation device 110 is mounted through its base 138, in some cases, one or more components of the manipulation device 110 (e.g., one or more sets of arm mechanisms and grasping mechanisms) can be secured directly through one or more articulation joints (e.g., articulation joints 136a-b).

In some cases, the system 100 can be configured to cleanse the user's body after the user has finished using the urinal 810 (e.g., after the user has finished urinating).

In some cases, the cleaning operation can include one or more of the following steps.

As shown in FIG. 8A, a user utilizes the urinal 810 by positioning himself within a space 814 of the urinal 810, such that he can urinate into the basin 812. When the user is finished using the urinal 810 (e.g., when the user has finished urinating), the user can request that he be cleaned by the system 100 (e.g., by manipulating a button or switch, vocalizing a command, or activating a motion sensor).

Prior to touching the user, the system 100 can place gloves onto one or more of its manipulating mechanisms (e.g., in a similar manner as described above). For example, the system 100 can guide the grasping mechanisms 140a-b towards a supply container 820 (e.g., by moving and/or reorienting one or more of its arm mechanisms and/or grasping mechanisms), and using the grasping mechanisms 140a-b, removes gloves from the supply container 820. The manipulating device 110 puts on the gloves by securing each glove with one of the grasping mechanisms 140a-b (e.g., by pinching the glove using two or more finger mechanisms), and guiding the other grasping mechanism 140a-b into the interior of the glove.

The system 100 can cleanse the user's body using moistened wipes (e.g., a portion of cloth or paper that has been moistened with water and/or a cleaning agent). The system 100 guides a grasping mechanism (e.g., the grasping mechanism 140a) to a container of moistened wipes 816 in the supply container 820. The grasping mechanism secures one of the moistened wipes 816 (e.g., by pinching the moistened wipe 816 using two or more finger mechanisms), and passes the moistened wipe 816 to another grasping mechanism (e.g., the grasping mechanism 140b). The grasping mechanism repeats some or all of the steps above to obtain one or more additional moistened wipes 816.

The system 100 guides a grasping mechanism (e.g., the grasping mechanism 140b) towards the user's body 824 (e.g., the user's groin or genital region), such that the moistened wipe 816 contacts the user's body 824. The system 100 then guides the grasping mechanism forwards and backwards and/or in a rotational motion one or more times, such that the moistened wipe 816 is wiped against the user's body 824.

The system 100 can dispose of the used moistened wipe 816 by rotating the grasping mechanism such that the moistened wipe 816 is facing downwards toward a waste receptacle 818, and releasing the moistened wipe 816 into the waste receptacle 818. The grasping mechanism can subsequently obtain an additional moistened wipe 816 (e.g., from another grasping mechanism), and repeat some or all of the steps above to further wipe the user's body. The system 100 can further notify the user that the cleaning process is complete (e.g., by emitting an auditory signal or message and/or displaying a visual signal or message).

The system 100 can also cleanse the user's body using water and/or a cleaning agent (e.g., soap). For example, the system 100 can cleanse the user's groin or genital region using water and/or soap.

In some cases, the washing operation can include one or more of the following steps.

Figure 8B:
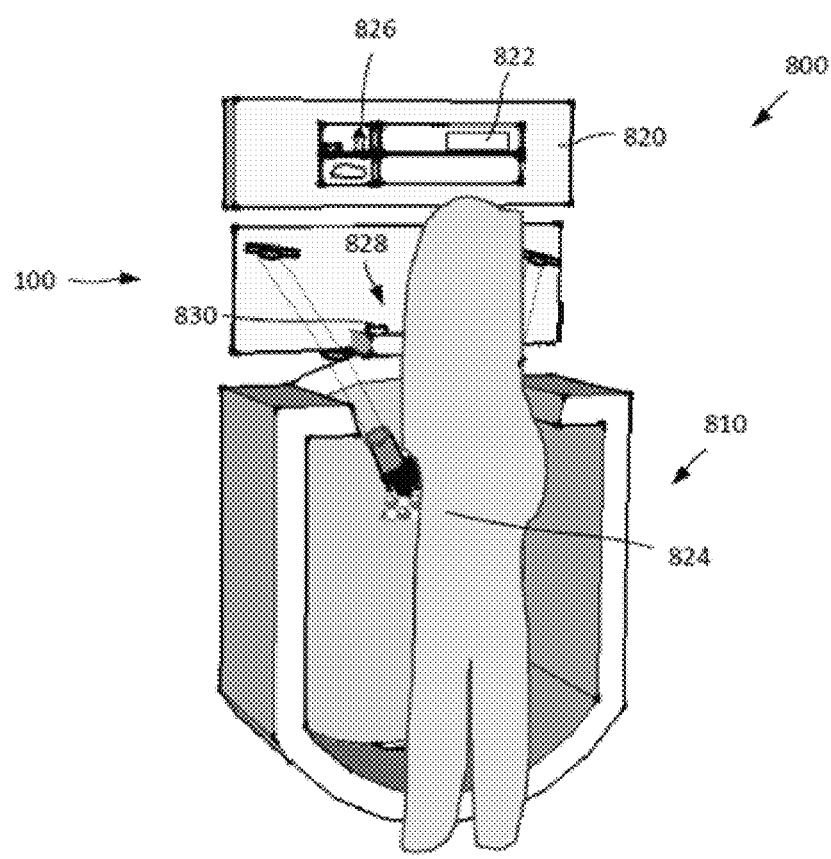

The system 100 guides a grasping mechanism to a soap dispenser 826, and obtains a portion of soap (e.g., by positioning the grasping mechanism beneath a spout of the soap dispenser with each of the finger mechanisms aligned together, and pressing on a dispensing mechanism to release soap from the spout onto the grasping mechanism). The system 100 guides the grasping mechanisms to the faucet 828, such that the dispensed soap is facing upward, and activates the faucet 828 (e.g., rotating a water release valve 830 with another grasping mechanism). Accordingly, the grasping mechanism is moistened with a mixture of soap and water. As shown in FIG. 8B, the system 100 positions the grasping mechanisms against a user's body 824 (e.g., the user's groin or genital region), and moves the grasping mechanisms against the user's body 824 (e.g., in a rotating and/or lengthwise motion), such that the user's body 824 is scrubbed by the grasping mechanisms. In some cases, the system 100 can articulate one or more of the finger mechanisms (e.g., curling and uncurling one or more finger mechanisms) and/or move one or more of the grasping mechanisms in a manner such that each of the surfaces of the user's body 824 is scrubbed (e.g., back surfaces, front surfaces, side surfaces, top surfaces, bottom surfaces, and so forth). The system 100 can further rinse the grasping mechanisms (e.g., to remove the soap) by positioning the grasping mechanisms under the 828 while it is dispensing water for a period of time. The system 100 can further rinse the user's body 824 by grasping the user's body 824, and positioning the user's body 824 under the faucet 828 while it is dispensing water for a period of time. The grasping mechanisms can subsequently repeat some or all of the steps above to further wash the user's body 824.

Further the system 100 can clean itself and/or the urinal 810 (e.g., in a similar manner as described above).

The system 100 dries the user's body by guiding a grasping mechanism to towel dispenser 822 (e.g., a paper towel dispenser) in the supply container 820, and grasping and removing a towel from the towel dispenser 822 (e.g., by pinching a towel using two or more finger mechanisms). The system 100 rubs the grasping mechanisms against the user's body, thereby drying the user's body. The towel can be disposed of in a waste receptacle 818 in a similar manner as described above. The grasping mechanisms can subsequently repeat some or all of the steps above to further dry the user's body.

In some cases, the system 100 can be configured to clean the urinal 810. As an example, the system 100 can be configured to operate the manipulation device 110 to scrub the urinal 810 with water and/or a cleaning agent (e.g., soap) and rinse the urinal 810.

In some cases, the cleaning operation can include one or more of the following steps.

The system 100 guides a grasping mechanism to towel dispenser 822 (e.g., a paper towel dispenser), and grasps and removes a towel from the towel dispenser 822 (e.g., by pinching a towel using two or more finger mechanisms). The system 100 dispenses a portion of soap onto the towel (e.g., by positioning the grasping mechanism such that the towel is positioned beneath a spout of the soap dispenser, and pressing on a dispensing mechanism to release soap from the spout onto the towel). The system 100 guides the grasping mechanism with the towel to the faucet 828, and activates the faucet (e.g., rotating a water release valve 830 with another grasping mechanism, such as the grasping mechanism 140*a*). Accordingly, the grasping mechanism is moistened with a mixture of soap and water. The system 100 guides the grasping mechanism with the towel to the urinal 810 (e.g., the basin 812, or any other surface of the urinal 810), rotates the grasping mechanism such that the towel is facing towards the surface of the urinal 810. The system 100 then guides the grasping mechanism forwards and backwards and/or in a rotating motion one or more times, such that the towel is wiped against the surface of the urinal 810. The grasping mechanism can subsequently repeat some or all of the steps above to further cleanse the urinal 810.

The system 100 can also dispose of the gloves on the grasping mechanisms (e.g., in a similar manner as described above) and/or clean itself (e.g., clean the grasping mechanisms using water and/or a cleaning agent in a similar manner as described above).

Upon completion, the system 100 can return the manipulating device 110 to its original position and/or orientation.

Figure 9:
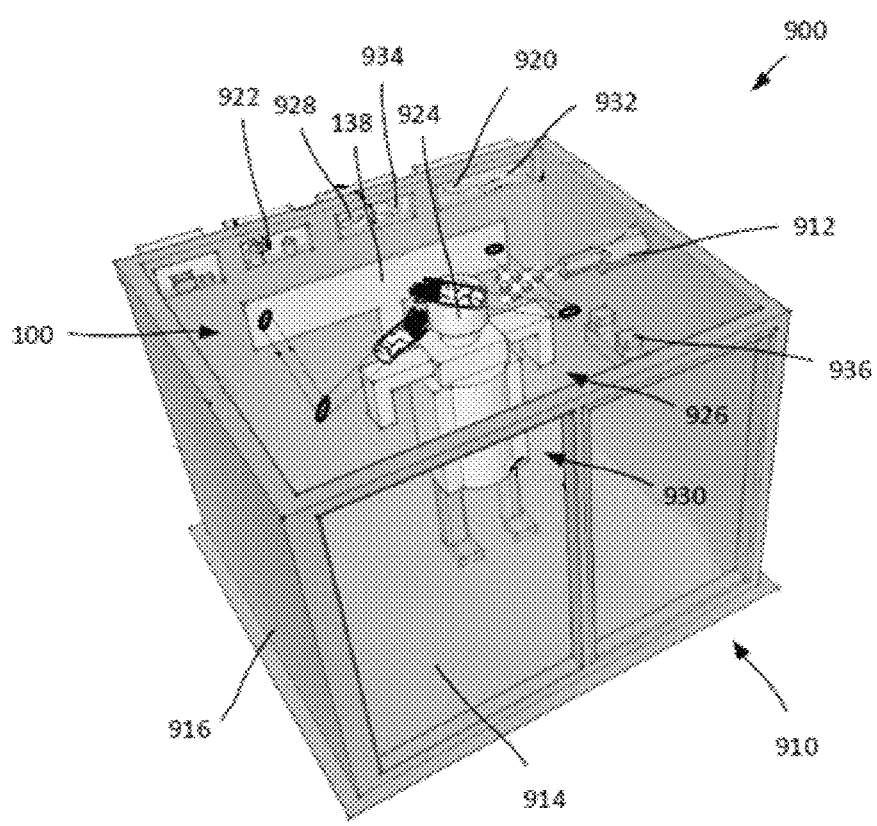
FIG. 9 is a diagram of an example system for washing and bathing a user.

In some cases, the system 100 can be used in conjunction with a shower to assist the user in washing and bathing his body. As an example, a system 900 for washing and bathing a user is shown in FIG. 9. The system 900 includes a shower 910 and a supply container 920. The system 900 also includes a system 100 for mimicking arm and hand movement (e.g., as shown and described with respect to FIGS. 1 and 2).

The shower 910 is an apparatus used for the cleaning and bathing of a user. The shower 910 includes a faucet 912 that dispenses water, and a basin 914 that collects water. The faucet 912 and the basin 914 are contained within an enclosure 916. In an example implementation, a user can stand in the enclosure 916 under the faucet 912, such that water dispensed by the faucet 912 flows over his body. Water is collected by the basin 914, and removed from the shower 910 (e.g., through a tube, pipe, or other conduit in fluid communication with a sewage or septic system), The supply container 920 contains objects or consumable items that facilitate use and/or maintenance of the system 900. For example, the supply container 820 can contain towels, cleaning agents (e.g., soap, shampoo, hair conditioners, disinfectants, bleach, cleaning solutions, cleaning powders, etc.), gloves, and so forth.

The system 900 also includes a system 100 for mimicking arm and hand movement. As described above, the system 100 can be similar to that shown and described with respect to FIGS. 1 and 2. For example, as shown in FIG. 9, the system 100 can include a first set of arm mechanisms 130*a* and 132*a*, grasping mechanism 140*a* having fingers mechanisms 144*a*, and articulating joints 134*a*, 136*a*, 142*a*, and 146*a* (referencing FIG. 1). In some cases, these two sets of components can mimic the functionality of two human arms and two human hands.

The system 100 can be mounted to the shower 910 or in proximity to the shower 910, such that the system 100 can access one or more of the components of the system 900. For example, as shown in FIG. 9, the system 100 can be mounted within the enclosure 916 of the shower 910.

Although an example position for the system 100 is shown, this is merely an illustrative example. In practice, the system 100 can be secured and/or positioned at different locations, depending on the implementation.

Further, although FIG. 9 shows an example in which the manipulation device 110 is mounted to the shower 910 through its base 138, in some cases, one or more components of the manipulation device 110 (e.g., one or more sets of arm mechanisms and grasping mechanisms) can be secured directly through one or more articulation joints (e.g., articulation joints 136*a-b*).

In some cases, the system 100 can be configured to wash and bathe the user's body. As an example, the system 100 can be configured to operate the manipulation device 110 to dispense a cleaning agent (e.g., soap, shampoo, hair conditioner, etc.) onto the user's body, scrub the user's body, rinse the user's body, and dry the user's body.

In some cases, the washing operation can include one or more of the following steps.

The user begins by removing his clothing, stepping into the shower 910, positioning his body such that it is between two of the grasping mechanisms, and operating the faucet 912 such that it dispenses a stream of water at the desired flow rate and temperature. The system can record the specified flow rate and temperature, such that the save settings are used in the future.

A user can initiate the washing operation by turning on or otherwise activating the system 100 (e.g., by manipulating a button or switch, vocalizing a command, or activating a motion sensor). In response, the manipulating device 110 unfolds its arm mechanisms 130*a-b* and 132*a-b*, such that they are extended away from the base 138. This can be performed, for example, by moving one or more of the arm mechanisms 130*a-b* and/or 132*a-b* with respect to the articulating joints 134*a-b*.

Prior to touching the user, the system 100 can place gloves onto one or more of its manipulating mechanisms (e.g., in a similar manner as described above). For example, the system 100 can guide the grasping mechanisms 140*a-b* towards a supply container 920 (e.g., by moving and/or reorienting one or more of its arm mechanisms and/or grasping mechanisms), and using the grasping mechanisms 140*a-b*, removes gloves from the supply container 920. The manipulating device 110 puts on the gloves by securing each glove with one of the grasping mechanisms 140*a-b* (e.g., by pinching the glove using two or more finger mechanisms), and guiding the other grasping mechanism 140*a-b* into the interior of the glove.

The system 100 can clean various parts of the user's body. For example, the system 100 washes the user's head by guiding the grasping mechanisms to a soap or shampoo dispenser 922 within the supply container 920, and obtains a portion of soap or shampoo. For example, the system 100 can position a grasping mechanism beneath a spout of the soap or shampoo dispenser with each of the finger mechanisms aligned together, press on a dispensing mechanism to release soap or shampoo from the spout onto the grasping mechanism. The system 100 guides the grasping mechanism towards the user's head 924, such that it contacts the user's head 924 and transfers the soap or shampoo to the user's head 924. As another example, the system 100 can guide a grasping mechanism to a soap or shampoo dispenser 922, position the soap or shampoo dispenser 922 above the user's head, and upend the soap or shampoo dispenser 922 for a period of time. The system 100 replaces the soap or shampoo dispenser 922 to its original storage location.

The system 100 spreads the soap and/or shampoo onto the user's head 924 by rubbing the grasping mechanisms against the user's head 924 in a forwards and backwards and/or rotating motion. In some cases, the grasping mechanisms can also clean the user's face and/or ears (e.g., by positioning one or more grasping mechanisms against the user's head and/or ears, and rubbing the grasping mechanisms against the user's head and/or ears). In some cases, the system 100 can insert one or more finger mechanisms in the user's ear to facilitate washing of the inner portions of the user's ear.

The grasping mechanisms can subsequently repeat some or all of the steps above to further wash the user's head 924.

The system 100 washes the user's upper body 926 (e.g., the user's upper members, neck, chest, abdomen, and back) by guiding the grasping mechanisms to a cleaning tool 928 (e.g., a sponge, luffa, or cleaning cloth), grasping the cleaning tool 928, and applying a portion of soap to the cleaning tool 928 (e.g., by positioning the cleaning tool 928 beneath a spout of the soap or shampoo dispenser 922, and pressing on a dispensing mechanism to release soap from the spout onto the cleaning tool 928). The system 100 guides the grasping mechanism towards the user's upper body 926, such that it contacts the user's upper body 926 and transfers the soap or shampoo to the user's upper body 926. As another example, the system 100 can guide a grasping mechanism to a bar of soap, and grasp the bar of soap. The system 100 guides the grasping mechanism towards the user's upper body 926, such that it contacts the user's upper body 926, and rubs the soap or to the user's upper body 926.

The system 100 spreads the soap onto the user's upper body 926 by rubbing the grasping mechanisms against the user's upper body 926 in a forwards and backwards and/or rotating motion. For example, the system 100 can use the grasping mechanisms to rub the user's upper members, neck, chest, abdomen, and/or back, such that soap is applied to one or more of those body parts.

The grasping mechanisms can subsequently repeat some or all of the steps above to further wash the user's upper body 926.

The system 100 washes the user's lower body 930 (e.g., the user's hip, thigh, leg, and foot) by guiding the grasping mechanisms to a cleaning tool 928, grasping the cleaning tool 928, and applying a portion of soap to the cleaning tool 928 (e.g., by positioning the cleaning tool 928 beneath a spout of the soap or shampoo dispenser 922, and pressing on a dispensing mechanism to release soap from the spout onto the cleaning tool 928). The system 100 guides the grasping mechanism towards the user's lower body 930, such that it contacts the user's lower body 930 and transfers the soap or shampoo to the user's lower body 930. As another example, the system 100 can guide a grasping mechanism to a bar of soap, and grasp the bar of soap. The system 100 guides the grasping mechanism towards the user's lower body 930, such that it contacts the user's lower body 930, and rubs the soap or to the user's lower body 930.

The system 100 spreads the soap onto the user's lower body 930 by rubbing the grasping mechanisms against the user's lower body 930 in a forwards and backwards and/or rotating motion. For example, the system 100 can use the grasping mechanisms to rub the user's hip, thighs, legs, and/or feet, such that soap is applied to one or more of those body parts.

The grasping mechanisms can subsequently repeat some or all of the steps above to further wash the user's lower body 930.

The system 100 can rinse the user's body by turning on the faucet 912 (e.g., rotating a water release valve 936 with a grasping mechanism), such that the user is bathed with water. The system 100 can also rinse the cleaning tool 928 (e.g., by positioning the cleaning tool 928 under the faucet 912 for a period of time), such that excess soap and/or shampoo is removed from the cleaning tool 928. The cleaning tool 928 can be returned to its original storage location after use.

The system 100 can dry the user's body. The system 100 guides a grasping mechanism to a towel 932 stored in the supply container 920, and grasping and removing a towel 932 (e.g., by pinching the towel 932 using two or more finger mechanisms). The system 100 rubs the towel 932 against the user's body, thereby drying the user's body. The grasping mechanism can subsequently repeat some or all of the steps above to further dry the user's body. The towel can be disposed of in a container (e.g., a laundry hamper) or placed back into the supply container 920 after use. The system 100 can further notify the user that the cleaning process is complete (e.g., by emitting an auditory signal or message and/or displaying a visual signal or message).

The system 100 can also clean the shower 910. The system guides a cleaning tool 934 (e.g., by pinching or gripping the cleaning tool 530 using two or more finger mechanisms). The cleaning tool 934 can be, for example, a brush, sponge, or scrubbing tool. The system 100 guides the cleaning tool 934 to a surface of the shower 910 (e.g., an interior surface of the enclosure 916), and moves the cleaning tool 934 in a rotating motion one or more times, such that the cleaning tool 934 is scrubbed against the shower 910.

In some cases, the system 100 can also apply a cleaning agent (e.g., soap, disinfectants, bleach, cleaning solutions, cleaning powders, etc.) to the cleaning tool 934 and/or shower 910 to facilitate cleaning of the shower 910. In some cases, this can be performed by positioning the cleaning tool 934 under a dispenser of a cleaning agent, and dispensing a portion of the cleaning agent onto the cleaning tool 934. In some cases, this can be performed by grasping a container of cleaning agent, and upending it over the cleaning tool 934 and/or within the shower 910 for a period of time, such that a portion of cleaning agent is dispensed.

The system 100 can also dispose of the gloves on the grasping mechanisms (e.g., in a similar manner as described above) and/or clean itself (e.g., clean the grasping mechanisms using water and/or a cleaning agent in a similar manner as described above).

Upon completion, the system 100 can return the manipulating device 110 to its original position and/or orientation.

Figure 11:
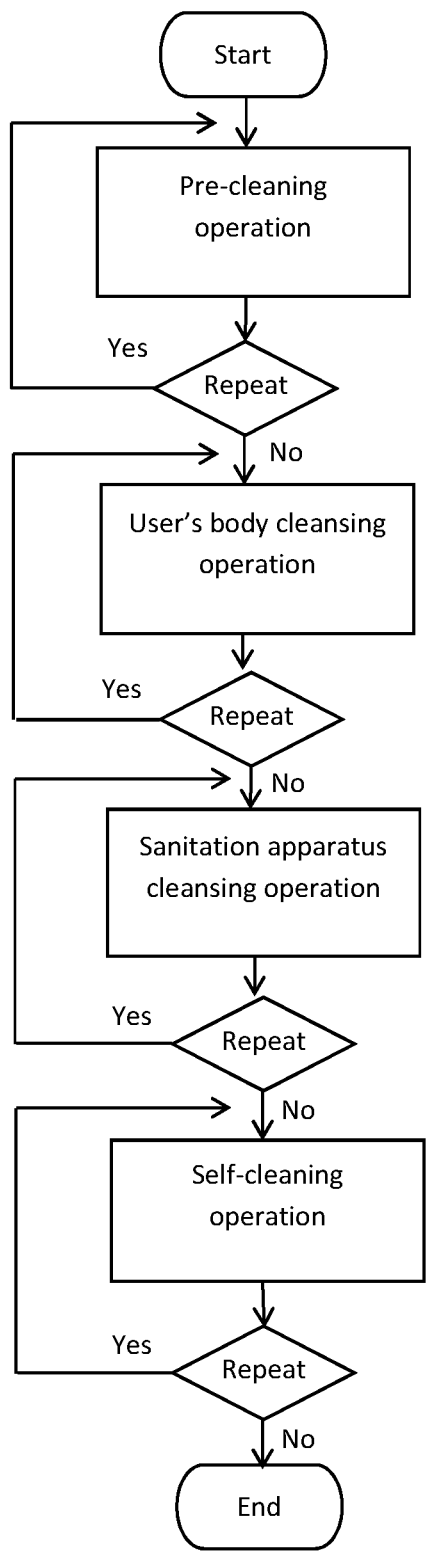
FIG. 11 is a flow diagram.

FIG. 11 is a flow diagram illustrating various functions of the control module. The flow diagram of FIG. 11 shows a pre-cleaning operation, an operation using a users body for cleansing, a sanitation apparatus cleansing operation, and a self-cleaning operation.

Figure 12:
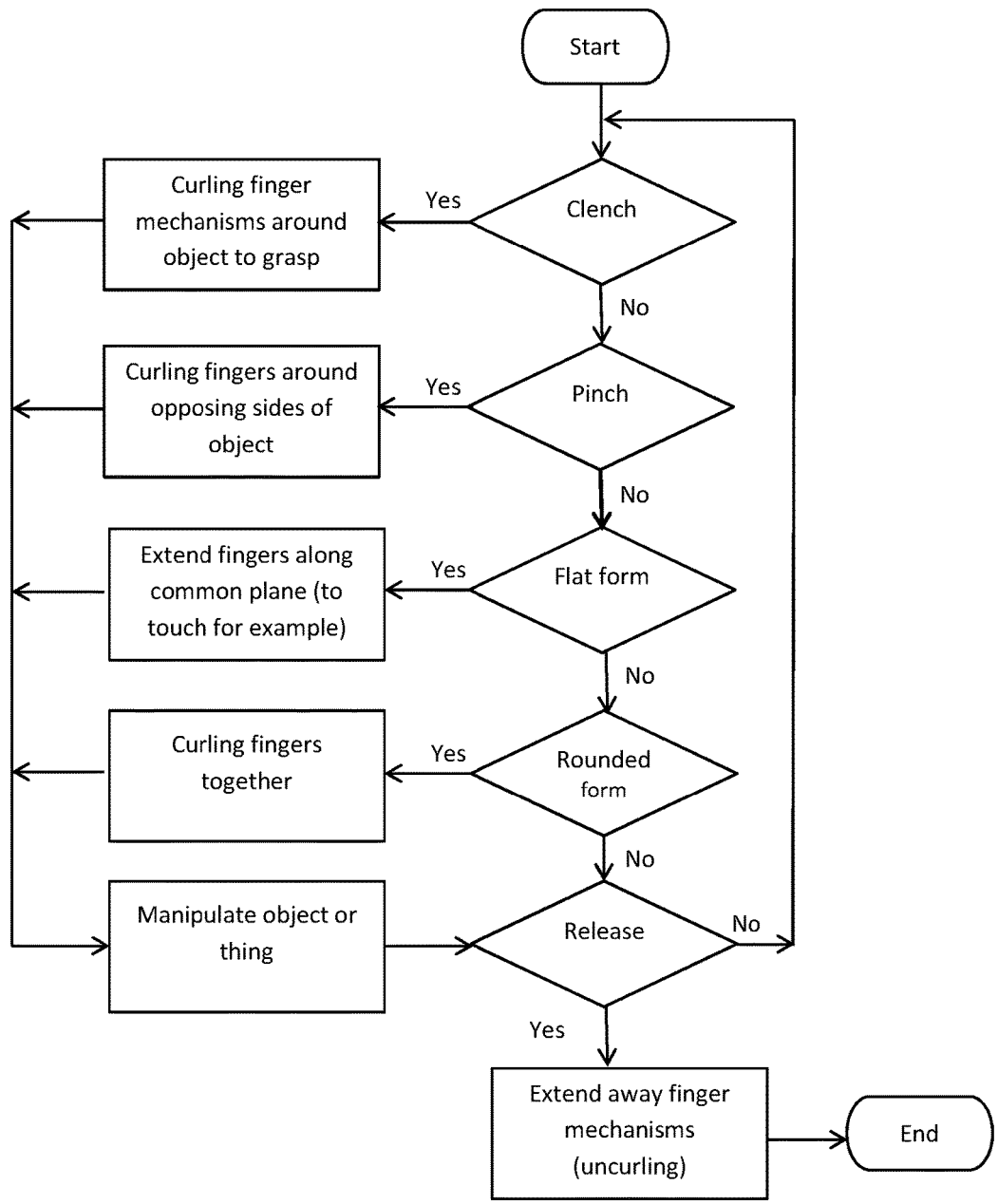
FIG. 12 is a flow diagram.

FIG. 12 is a flow diagram illustrating various functions of the grasping mechanism. The flow diagram of FIG. 12 shows a clench decision, a pinch decision, a flat form decision, a rounded form decision and a release decision. The flow diagram of FIG. 12 also includes a step of curling a finger mechanism around an object to grasp, a step of curling fingers around opposing sides of an object, a step of extending fingers along a common plane, a step of curling fingers together, and a step of manipulating an object or thing. A step of extending away finger mechanisms is also shown.

Although example steps are described herein, these are merely illustrative examples. In practice, the systems described herein can perform other steps, either instead of or in addition to those described herein. Further, although example movements are described with respect to particular components, these are also merely illustrative examples. Other types of movements can also be performed and/or other components can also be moved to achieve particular results.

Further, although example body parts are described herein (e.g., a user's posterior, hands, face, etc.), it is understood that implementations of the system 100 can perform one or more of the operations described herein with respect to any part of a person's body. As an example, implementations of the system 100 can be configured to clean, wipe, dry, scrub, and/or perform any other function with respect to other body parts (e.g., feet, legs, stomach, chest, knees, arms, etc.) Similarly, although example objects are described herein (e.g., towels, wipes, toilet tissue, etc.), it is understood that implementations of the system 100 can perform one or more of the operations described herein with respect to any other object (e.g., toothbrushes, combs, cups, dental floss, etc.).

Further, although example steps are described herein, these steps need not be performed in the order that they are described. In some cases, one or more steps can be performed in a different order, or not performed at all. Further still, any of the steps can be repeated any number of times, either individually or as one of a group of repeated steps, to achieve a particular result. For example, one or more steps corresponding to a cleaning function can be repeated to further clean a particular object or surface. As another example, one or more steps corresponding to a drying function can be repeated to further dry a particular object or surface.

Although various implementations are described above, these are merely illustrative examples. In practice, implementations of the system 100 can be used to perform any physical task in a manner that mimics a user's arms and hands. For example, in some cases, implementations of the system 100 can also be used in assist a user in cleaning dishes, cooking, cleaning a floor, folding and ironing clothes, and/or driving. For example, the system 100 can provide one or more sets of arm mechanisms, grasping mechanism having fingers mechanisms, and articulating joints, and use each of those sets to mimic the functionality of a human arm and hand. In turn, the system 100 can direct the components to perform tasks that might otherwise be performed manually by a user's own arms and hands.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the control module 120 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 10:
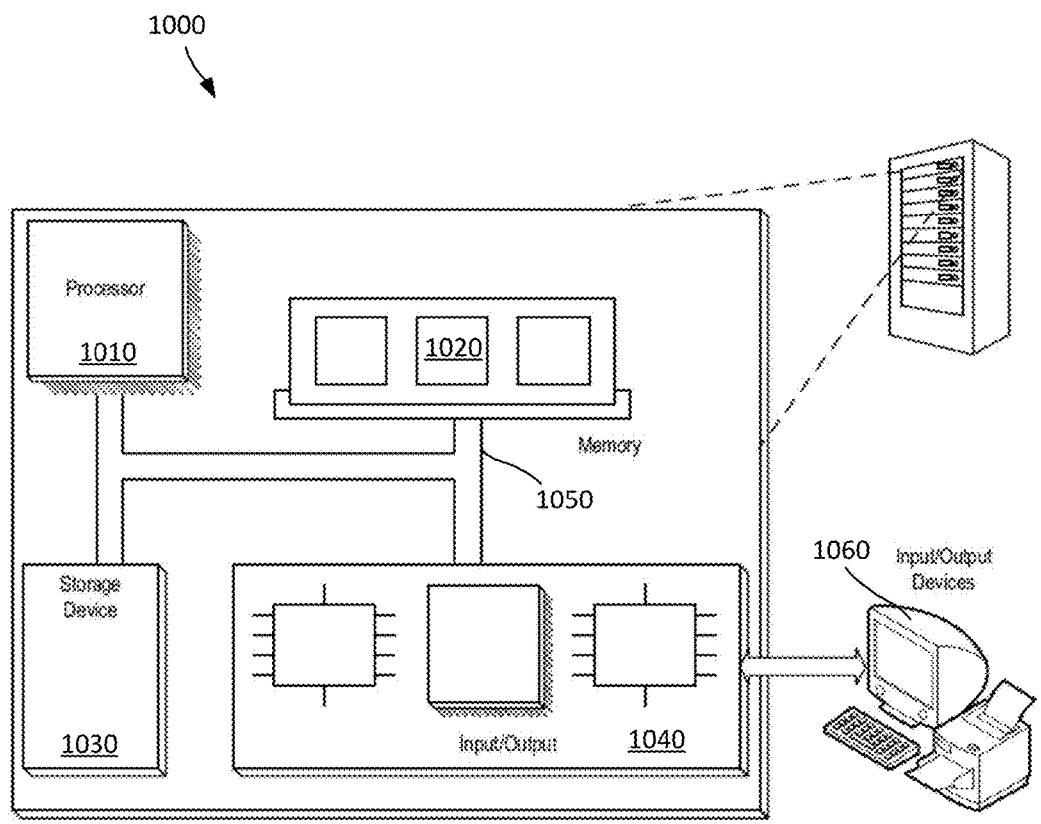
FIG. 10 is a diagram of a computer system.

FIG. 10 shows an example computer system 1000 that includes a processor 1010, a memory 1020, a storage device 1030 and an input/output device 1040. Each of the components 1010, 1020, 1030 and 1040 can be interconnected, for example, by a system bus 1050. The processor 1010 is capable of processing instructions for execution within the system 1000. In some implementations, the processor 1010 is a single-threaded processor, a multi-threaded processor, or another type of processor. The processor 1010 is capable of processing instructions stored in the memory 1020 or on the storage device 1030. The memory 1020 and the storage device 1030 can store information within the system 1000.

The input/output device 1040 provides input/output operations for the system 800. In some implementations, the input/output device 1040 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1060. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

What is claimed is:

1. A system comprising:
    a manipulation device configured to be mounted to a sanitation apparatus for storing or disposing human waste, the manipulation device comprising:
    a first arm mechanism,
    a second arm mechanism,
    a first articulating joint mechanically coupling the first arm mechanism to the second arm mechanism,
    a grasping mechanism, and
    a second articulating joint mechanically coupling the second arm mechanism to the grasping mechanism;
    a touch-sensitive detection sensor configured to monitor the contact of the manipulation device with an object or the physical environment; and
    a control module communicatively coupled to the manipulation device and configured to control the manipulation device to perform:
    a pre-cleaning operation to prepare the sanitation apparatus for use,
    a user cleansing operation to cleanse a user's body after use of the sanitation apparatus by the user,
    a sanitation apparatus cleansing operation to cleanse the sanitation apparatus after use of the sanitation apparatus by the user, and
    a self-cleansing operation to cleanse the manipulation device.

2. The system of claim 1, wherein performing the user cleansing operation comprises:
    grasping a first wiping sheet with the grasping mechanism;
    positioning the first wiping sheet against a part of a user's body;
    dragging the first wiping sheet one or more times against the part of the user's body; and
    releasing the first wiping sheet into a basin of the sanitation apparatus.

3. The system of claim 2, wherein performing the user cleansing operation comprises:
    grasping a second wiping sheet with the grasping mechanism, the second wiping sheet being moistened with a first cleaning agent;

positioning the second wiping sheet against the part of the user's body;
dragging the second wiping sheet one or more times against the part of the user's body; and
releasing the second wiping sheet into the basin of the sanitation apparatus.

4. The system of claim 3, wherein performing the user cleansing operation comprises:
grasping a third wiping sheet with the grasping mechanism, wherein the third wiping sheet is substantially dry;
positioning the third wiping sheet against the part of the user's body;
dragging the third wiping sheet one or more times against the part of the user's body;
releasing the third wiping sheet into the basin of the sanitation apparatus; and
operating a flushing mechanism of the sanitation apparatus.

5. The system of claim 1,
wherein performing the pre-cleaning operation comprises:
grasping a seat cover of the sanitation apparatus with the grasping mechanism,
unfolding the seat cover with the grasping mechanism, and
placing the seat cover onto a seating surface of the sanitation apparatus, and
wherein performing the sanitation apparatus cleansing operation comprises:
grasping a seat cover with the grasping mechanism,
releasing the seat cover into a basin of the sanitation apparatus,
adding a cleaning solution into the basin of the sanitation apparatus,
grasping a cleaning tool with the grasping mechanism,
dragging the cleaning tool one or more times across one or more surfaces of the sanitation apparatus, and
operating a flushing mechanism of the sanitation apparatus, and
wherein performing the self-cleansing operation comprises:
moistening the grasping mechanism with a mixture of soap and water,
scrubbing the grasping mechanism,
positioning the grasping mechanism under a faucet,
rinsing the grasping mechanism,
grasping a towel with the grasping mechanism,
rubbing the grasping mechanism against the towel, and
releasing the towel in a waste receptacle.

6. The system of claim 1, wherein the control module is further configured to repeat at least one of the pre-cleaning operation, the user cleansing operation, the sanitation apparatus cleansing operation, or the self-cleansing operation one or more times.

7. The system of claim 1, wherein the grasping mechanism comprises one or more articulating fingers.

8. The system of claim 1, wherein the first arm mechanism is configured to be mounted to the sanitation apparatus through a third articulating joint.

9. The system of claim 8, wherein the manipulation device further comprises:
a third arm mechanism,
a fourth arm mechanism,
a fourth articulating joint mechanically coupling the third arm mechanism to the fourth arm mechanism,
a second grasping mechanism, and
a fifth articulating joint mechanically coupling the fourth arm mechanism to the second grasping mechanism.

10. The system of claim 9, wherein the manipulation device further comprises a sixth articulating joint, and wherein the third arm mechanism is configured to be mounted to the sanitation apparatus through the sixth articulating joint.

11. The system of claim 1, wherein the manipulation device is mounted above a basin of the sanitation apparatus.

12. The system of claim 1, wherein the control module comprises an electronic control module configured to transmit electronic control signals to the manipulation device, and
wherein the manipulation device is configured to automatically operate in response to receiving the electronic control signals.

13. The system of claim 1, wherein the control module comprises a mechanical mechanism, and
wherein the manipulation device is configured to operate in response to a user manipulating the mechanical mechanism.

14. The system of claim 1, wherein the sanitation apparatus is a toilet.

15. The system of claim 1, wherein the sanitation apparatus is a urinal.

* * * * *